US011845916B2

(12) United States Patent
Mui

(10) Patent No.: US 11,845,916 B2
(45) Date of Patent: Dec. 19, 2023

(54) BURSTABLE SPORICIDAL CLEANING WIPE SYSTEM CONTAINING STABILIZED HYPOCHLORITE

(71) Applicant: THE CLOROX COMPANY, Oakland, CA (US)

(72) Inventor: Timothy P. Mui, Pleasanton, CA (US)

(73) Assignee: THE CLOROX COMPANY, Oakland, CA (US)

( * ) Notice: Subject to any disclaimer, the term of this patent is extended or adjusted under 35 U.S.C. 154(b) by 472 days.

(21) Appl. No.: 16/911,234

(22) Filed: Jun. 24, 2020

(65) Prior Publication Data

US 2021/0403833 A1 Dec. 30, 2021

(51) Int. Cl.
| | |
|---|---|
| C11D 1/825 | (2006.01) |
| C11D 3/48 | (2006.01) |
| C11D 17/04 | (2006.01) |
| C11D 3/395 | (2006.01) |
| C11D 1/83 | (2006.01) |
| C11D 1/37 | (2006.01) |
| A61L 2/18 | (2006.01) |
| B08B 1/00 | (2006.01) |
| B08B 3/08 | (2006.01) |
| A61L 2/26 | (2006.01) |
| C11D 1/75 | (2006.01) |
| C11D 1/14 | (2006.01) |
| C11D 1/22 | (2006.01) |

(52) U.S. Cl.
CPC ....... *C11D 3/48* (2013.01); *A61L 2/18* (2013.01); *A61L 2/26* (2013.01); *B08B 1/006* (2013.01); *B08B 3/08* (2013.01); *C11D 1/37* (2013.01); *C11D 1/83* (2013.01); *C11D 3/3953* (2013.01); *C11D 17/046* (2013.01); *C11D 17/049* (2013.01); *A61L 2202/17* (2013.01); *C11D 1/146* (2013.01); *C11D 1/22* (2013.01); *C11D 1/75* (2013.01)

(58) Field of Classification Search
CPC .... C11D 1/72; C11D 1/75; C11D 3/22; C11D 3/48; C11D 3/395; C11D 3/3951; C11D 17/049
See application file for complete search history.

(56) References Cited

U.S. PATENT DOCUMENTS

| | | |
|---|---|---|
| 3,749,672 A | 7/1973 | Golton et al. |
| 3,929,678 A | 12/1975 | LAughlin et al. |
| 3,985,668 A | 10/1976 | Hartman |
| 4,259,217 A | 3/1981 | Murphy |
| 5,462,689 A | 10/1995 | Choy et al. |
| 5,821,214 A | 10/1998 | Weibel |
| 5,908,707 A | 6/1999 | Cabell et al. |
| 5,988,371 A | 11/1999 | Paley et al. |
| 6,001,187 A | 12/1999 | Paley et al. |
| 6,022,840 A | 2/2000 | Weibel |
| 6,036,789 A | 3/2000 | Weibel |
| 6,068,820 A | 5/2000 | De Guzman |
| 6,162,371 A | 12/2000 | Rees et al. |
| 6,228,824 B1 | 5/2001 | Gorlin |
| 6,245,361 B1 | 6/2001 | Merritt |
| 6,448,215 B1 | 9/2002 | Grande et al. |
| 6,471,974 B1 | 10/2002 | Rees et al. |
| 6,649,581 B1 | 11/2003 | Lalle et al. |
| 6,825,159 B2 | 11/2004 | Man et al. |
| 6,827,792 B2 | 12/2004 | Cervero et al. |
| 6,866,145 B2 | 3/2005 | Richards et al. |
| 6,998,379 B1 | 2/2006 | Costagliola |
| 7,008,600 B2 | 3/2006 | Katsigras et al. |
| 7,070,737 B2 * | 7/2006 | Bains ............... A61L 2/232 424/661 |
| 7,390,775 B2 | 6/2008 | Rees et al. |
| 7,592,301 B2 | 9/2009 | Smith et al. |
| 7,807,118 B2 | 10/2010 | Green et al. |
| 7,967,220 B2 | 6/2011 | Hansen et al. |
| 8,066,444 B2 | 11/2011 | Rippl et al. |
| 8,318,654 B2 | 11/2012 | Hoffman et al. |

(Continued)

FOREIGN PATENT DOCUMENTS

| | | |
|---|---|---|
| AU | 7054287 A | 9/1987 |
| AU | 2000043983 | 11/2000 |

(Continued)

OTHER PUBLICATIONS

Quaternium-27, SAAPedia Surfactant, http://www.saapedia.org/en/saa/?type=detail&id=3780, Jan. 10, 2023.
Rutala et al., "Uses of Inorganic hypochlorite (Bleach) in Health-Care Facilities", clinical microbioogy review (1997) vol. 10, No. 4, pp. 597-610, http://rutalapdf.web.unc.edu/files/2015/08/Rutala-1997-Usesof-inorganic-hypochlorite-bl.pdf.
Final Office Action received for U.S. Appl. No. 17/096,852, dated Jul. 14, 2022, 12 pages.
Non-Final Office Action received for U.S. Appl. No. 17/096,816, dated Oct. 18, 2022, 10 pages.
Non-Final Office Action received for U.S. Appl. No. 17/096,852, dated Feb. 2, 2022, 10 pages.

(Continued)

*Primary Examiner* — Charles I Boyer
(74) *Attorney, Agent, or Firm* — WORKMAN NYDEGGER

(57) ABSTRACT

Sanitizing and disinfecting compositions with relatively low levels of free available chlorine, with good effectiveness against microbes, included in a burstable pouch of a system also including a plurality of initially undosed (e.g., dry) wipes in a resealable package thereof. The composition may include less than 0.5% by weight hypochlorite or other free available chlorine level, with a pH less than 12. The composition is long term stable in the pouch, but upon bursting of the pouch and dosing of the wipes, exhibits only short-term stability. Because of the low level of hypochlorite, the dosed wipes exhibit improved surface compatibility and negligible "bleach" odor, while providing at least a 3-log reduction in *C. diff* population within 10 minutes.

10 Claims, 9 Drawing Sheets

(56) References Cited

U.S. PATENT DOCUMENTS

| | | |
|---|---|---|
| 8,642,054 B2 | 2/2014 | Green |
| 8,701,880 B2 | 4/2014 | Noel |
| 8,755,114 B1 | 6/2014 | Tanner et al. |
| 8,765,114 B2 | 7/2014 | Scheuing et al. |
| 8,859,481 B2 | 10/2014 | Clark et al. |
| 8,894,907 B2 | 11/2014 | Privitera et al. |
| 8,915,359 B2 | 12/2014 | DiLiberto et al. |
| 9,828,143 B2 | 11/2017 | Nathan |
| 10,279,978 B2 | 5/2019 | DiLiberto et al. |
| 10,457,465 B2 | 10/2019 | Shabanova et al. |
| 10,986,841 B2 | 4/2021 | MacNaughtan et al. |
| 11,596,152 B2 | 3/2023 | MacNaughtan et al. |
| 2003/0022941 A1 | 1/2003 | Taylor et al. |
| 2003/0155549 A1 | 8/2003 | Yoshikawa et al. |
| 2005/0008575 A1 | 1/2005 | Liu |
| 2005/0008576 A1 | 1/2005 | Makansi |
| 2005/0025668 A1* | 2/2005 | Katsigras ............. C11D 3/3956 424/661 |
| 2005/0155630 A1 | 7/2005 | Kilkenny et al. |
| 2005/0202491 A1 | 9/2005 | Nelson et al. |
| 2005/0282722 A1 | 12/2005 | McReynolds et al. |
| 2006/0089285 A1 | 4/2006 | Ahmed et al. |
| 2006/0278586 A1 | 12/2006 | Nalepa et al. |
| 2008/0167211 A1 | 7/2008 | Pivonka et al. |
| 2008/0305183 A1 | 12/2008 | Croud et al. |
| 2009/0016990 A1 | 1/2009 | Alberte et al. |
| 2009/0050179 A1 | 2/2009 | Kang et al. |
| 2009/0143481 A1 | 6/2009 | Man et al. |
| 2010/0305013 A1* | 12/2010 | Hanifl ................. C11D 3/3947 510/133 |
| 2011/0045187 A1 | 2/2011 | McCloskey |
| 2013/0028990 A1 | 1/2013 | Smith et al. |
| 2013/0216293 A1 | 8/2013 | Garner et al. |
| 2013/0280349 A1* | 10/2013 | Kimler ................... A01N 59/00 424/723 |
| 2014/0117278 A1 | 5/2014 | Cawlfield et al. |
| 2014/0134224 A1 | 5/2014 | Mallet et al. |
| 2014/0328946 A1 | 11/2014 | Northey |
| 2015/0030528 A1 | 1/2015 | Xu |
| 2015/0133361 A1* | 5/2015 | Scheuing ............. C11D 3/3418 510/367 |
| 2015/0306266 A1 | 10/2015 | Burke et al. |
| 2017/0208812 A1* | 7/2017 | Som ........................ A61L 2/18 |
| 2018/0282048 A1 | 10/2018 | Hayman et al. |
| 2018/0344122 A1 | 12/2018 | Kang et al. |
| 2018/0361175 A1 | 12/2018 | Xu et al. |
| 2019/0023476 A1* | 1/2019 | Shabanova ........ B65D 75/5838 |
| 2019/0023477 A1 | 1/2019 | Kelley et al. |
| 2020/0063077 A1* | 2/2020 | Nolan ................... D21H 27/02 |
| 2020/0138034 A1* | 5/2020 | Macnaughtan ........ C11D 1/662 |
| 2021/0059257 A1 | 3/2021 | MacNaughtan et al. |
| 2021/0059258 A1 | 3/2021 | MacNaughtan et al. |

FOREIGN PATENT DOCUMENTS

| | | |
|---|---|---|
| AU | 2012264486 A1 | 10/2013 |
| CN | 1242797 A | 1/2000 |
| EP | 1130083 A1 | 9/2001 |
| EP | 1281320 A1 | 2/2003 |
| EP | 1550468 A1 | 7/2005 |
| RU | 2522865 C1 | 7/2014 |
| WO | 97/43392 A1 | 11/1997 |
| WO | 98/11776 A1 | 3/1998 |
| WO | 2004/108091 A2 | 12/2004 |
| WO | 2007/065533 A1 | 6/2007 |
| WO | 2010/046142 A2 | 4/2010 |
| WO | 2013/032951 A1 | 3/2013 |
| WO | 2013/032961 A1 | 3/2013 |
| WO | 2013/171343 A2 | 11/2013 |
| WO | 2014/127713 A1 | 8/2014 |

OTHER PUBLICATIONS

Notice of Allowance and Fees Due (PTOL-85) dated Apr. 14, 2023 for U.S. Appl. No. 17/096,816, 10 page(s).

Notice of Allowance received for U.S. Appl. No. 17/096,852, dated Nov. 2, 2022, 11 pages.

Pentaethylene glycol monododecyl ether Sigma-Aldrich catalog, accessed Jan. 30, 2020 (Year: 2020).

* cited by examiner

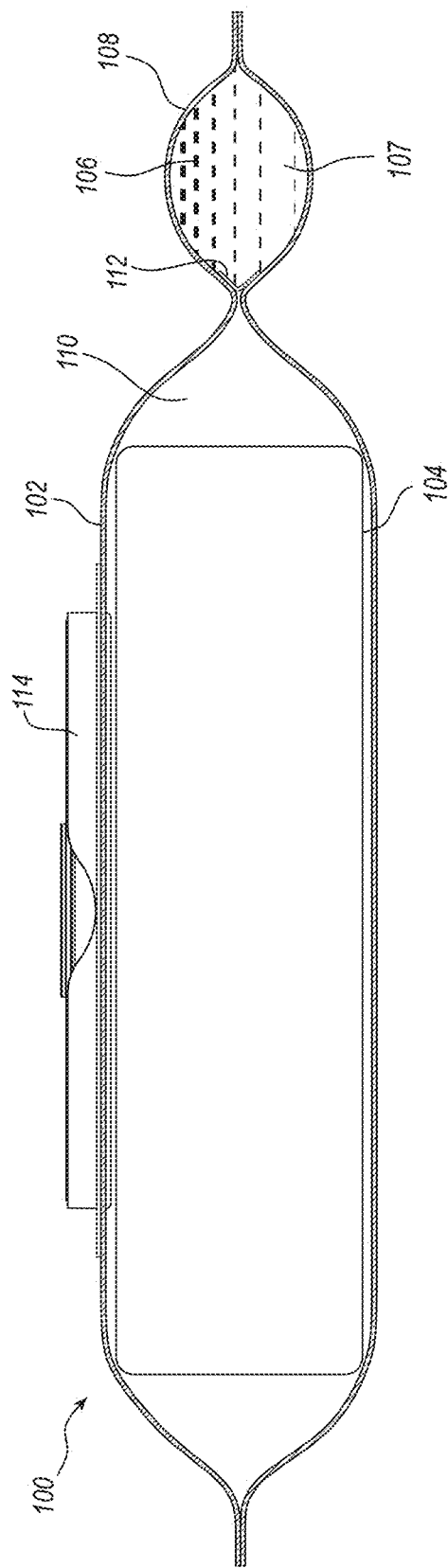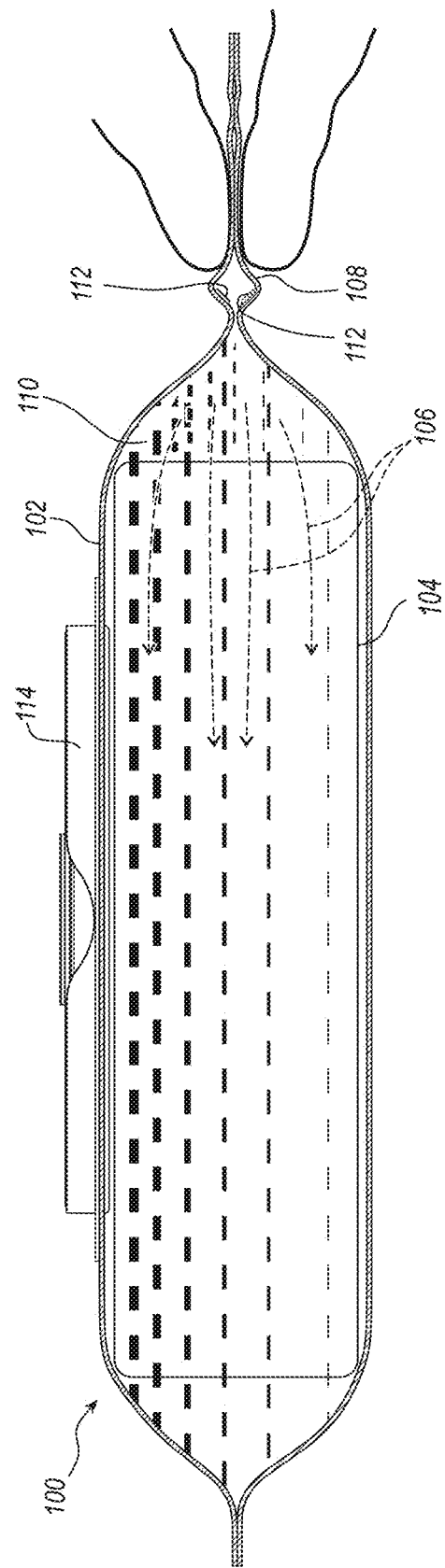
FIG. 1E
FIG. 1F

BURSTABLE SPORICIDAL CLEANING WIPE SYSTEM CONTAINING STABILIZED HYPOCHLORITE

BACKGROUND OF THE INVENTION

1. The Field of the Invention

The present invention relates to systems for delivering liquid compositions including active chlorine species (e.g., a hypohalite), for example, as used to sanitize, disinfect, clean, or otherwise treat a surface.

2. Description of Related Art

Sodium hypochlorite is a highly effective cleaning, bleaching and sanitizing agent that is widely used in cleaning and sanitizing various hard and soft surfaces, etc. In order to achieve efficacy against various microorganisms (e.g., particularly *Clostridium difficile* ("*C. diff*") or tuberculosis ("TB")), existing bleach compositions have typically required the inclusion of at least 0.5% bleach in the formulation, particularly in order to be effective against spores of such microorganisms. Inclusion of less bleach has not typically been reliable against such microorganisms or their spores, particularly while also providing adequate shelf life for the product.

While such existing formulations can be relatively effective against target microorganisms, the inclusion of the relatively high concentrations of hypochlorite bleach components in existing formulations results in damage to hard and soft surfaces to which such compositions are applied. In addition, the characteristic "bleach" odor associated with such compositions is also often a problem. Some healthcare workers are hesitant to use such bleach compositions for application to a wide variety of surfaces and environments because they have concerns about surface damage and overwhelming bleach odor. Healthcare workers may use such compositions to treat an area where a patient who was known to be infected has been (e.g., an isolation room), but such workers are often hesitant to use such bleach compositions more broadly, for general prevention of a disease outbreak. In order to better prevent outbreaks, and rather than just react to such outbreaks, all surfaces in such a healthcare setting should be treated with the most effective composition available, but as a practical matter other considerations such as surface compatibility and overall aesthetics of the product exert a heavy influence on what compositions are used, and when.

As such, there continues to be a need for systems that could provide good microefficacy against target microorganisms, at very low active chlorine concentrations (e.g., less than 0.5% by weight), while maintaining adequate stability (e.g., 1 year shelf stable) for the system as a whole, as manufactured. Development of such systems that include a composition having low free active chlorine concentration, exhibiting good microefficacy, and a long shelf-life for the system as a whole, would be particularly advantageous as this would allow application of such compositions more broadly to a wider variety of surfaces, and environments, due to improved surface compatibility and less (e.g., even negligible) "bleach" odor.

BRIEF SUMMARY OF THE INVENTION

While one may consider decreasing the amount of hypohalite (e.g., hypochlorite) or other source of free available halide (e.g., free available chlorine) in such a formulation to present a solution to the above problems, conventional wisdom teaches that decreasing the amount of hypochlorite or other free available chlorine concentration will have a large negative impact on the microefficacy of the formulation. Furthermore, while it is generally known that decreasing pH can increase microefficacy, such decreases in pH are also associated with substantially decreased shelf-stability of the formulation, particularly in the presence of organic surfactants. This presents a significant challenge to provide a formulation, which would have lower hypochlorite or other free available halide concentration (e.g., less than 0.5%), while still providing at least a 12-month shelf life, and also achieving efficacy against *C. diff*, TB, or other target microorganisms.

Furthermore, providing such compositions already pre-dosed on a wipe (e.g., a nonwoven wipe) is desirable from the perspective of ease of use, but this can also greatly affect microefficacy. For example, where such compositions are dosed onto such a wipe or other substrate, the composition as squeezed from the substrate (i.e., the squozate) is not the same as that which was loaded into the substrate because the substrate often binds or otherwise inactivates some of the hypohalite or other active in the composition dosed onto the substrate. Such interactions negatively affect the microefficacy of the system as a whole. Because of similar interactions between the composition and the substrate, the composition also often exhibits significantly reduced stability once dosed onto the substrate. For example, while a given composition on its own may exhibit an acceptable shelf life of a year or more, the same composition as loaded onto a substrate may now only exhibit a shelf life that is far shorter, e.g., such as less than 6 months, less than 1 month, or in some circumstances, even less than 1 day. It would be advantageous to provide a system that could provide wipes dosed with a sanitizing or disinfecting composition, which was formulated to have low "bleach" odor characteristics and improved surface compatibility (e.g., about 0.05-0.5% free available chlorine), but where the system at the same time could provide an acceptable shelf life to the system as a whole (e.g., at least 6 months, or at least 1 year). The present invention provides such a system.

In one embodiment, the present invention is directed to a system for sanitizing or disinfecting, where the system includes a package containing a plurality of wipes that are initially undosed, and a sanitizing or disinfecting composition within a burstable pouch of the package, configured to dose the undosed wipes with the composition upon bursting of the pouch. The composition includes less than 0.5% by weight of hypohalite (e.g., hypochlorite) or other free available halide (e.g., chlorine). The composition may have a pH of less than 12 (e.g., from 11 to 11.5). The composition as used once dosed on the wipe may provide at least a 3-log reduction in a *C. diff* or other target population within 10 minutes (e.g., within 5 minutes, within 3 minutes).

One or more surfactants may be included in the composition. For example, applicant has unexpectedly discovered that surfactant selection in such compositions including very low free available chlorine can be at least as important as pH or other characteristics for driving stability and microefficacy. Applicant has found that inclusion of nonionic and/or zwitterionic surfactants in particular may greatly enhance microefficacy, and allow for some relative reduction in pH, while maintaining desired stability characteristics. Anionic surfactants may actually interfere with the ability to provide such results, and as such, may be limited or excluded from the formulation. The present systems provide a composition that exhibits improved aesthetics (e.g., odor) and surface compatibility, for dosing onto one or more wipes or other substrates just before initial use of the pack or other container of wipes, which provides the above-described benefits, while also being effective against *C. diff*, TB or other target microbes, including spores thereof.

This effect of surfactant package selection was surprisingly found to be so strong that it controlled whether the formulation passed applicable EPA TB kill tests or not, independent of hypochlorite concentration. Such discovery has allowed Applicant to provide specific formulations that include only very low levels of hypochlorite or other free available chlorine, addressing issues with odor and surface compatibility, while at the same time providing microefficacy against TB, *C. diff*, or other desired target organisms.

The composition may have an R value that is greater than 0 (e.g., at least 0.5, or equal to 1), where R value is defined as the sum of the concentration of "good" nonionic, zwitterionic, and cationic surfactants (or chaotropes) divided by total surfactant (including any chaotropes, and/or any surfactant aids) concentration. The term "surfactant" is used herein broadly, for simplicity, and includes such chaotropes or other components included principally for reducing surface tension. The composition as delivered from a dosed wipe of the system may exhibit at least a 3-log reduction against one or both of *C. diff* or the TB causing bacteria *Mycobacterium bovis* within 10 minutes (e.g., 2-10 minutes, 3-7 minutes, or 3-5 minutes).

The composition for dosing the wipes advantageously includes less sodium hypochlorite or other free available halide than typical existing formulations, e.g., often only 0.4% or less (e.g., 0.2% to 0.3%), so as to be less likely to cause unwanted surface damage, or exhibit an undesirable "bleach" odor during use. Such compositions may thus exhibit increased compatibility to be more useful across a wide variety of environments and uses. The concentration of hypochlorite or other free available halide may be even less than the above values, as delivered in the squozate (i.e., as squeezed from the wipe), e.g., due to interactions between the wipe and the composition.

Another embodiment is directed to a system for sanitizing or disinfecting comprising a re-sealable package containing a plurality of initially dry wipes, and a sanitizing or disinfecting composition including from 0.05% to less than 0.5% (e.g., 0.2% to 0.3%) by weight of hypochlorite or other free available chlorine, at least one nonionic or zwitterionic surfactant, where the R value as defined above is greater than 0, where the composition has a pH from 8.5 to 11.8, and where the composition may exhibit at least a 3-log reduction in *C. diff* within 10 minutes, or within 5 minutes, or within 3 minutes. In this embodiment, the composition may be free of anionic surfactants.

Further features and advantages of the present invention will become apparent to those of ordinary skill in the art in view of the detailed description of preferred embodiments below.

BRIEF DESCRIPTION OF THE DRAWINGS

To further clarify the above and other advantages and features of the present invention, a more particular description of the invention will be rendered by reference to specific embodiments thereof, which are illustrated in the drawings located in the specification. It is appreciated that these drawings depict only typical embodiments of the invention and are therefore not to be considered limiting of its scope. The invention will be described and explained with additional specificity and detail through the use of the accompanying drawings.

FIGS. 1E-1F schematically illustrate how the burstable pouch containing the sanitizing or disinfecting composition may be activated, delivering the composition into that portion of the package that includes the initially undosed wipes or dry wipes.

DETAILED DESCRIPTION OF THE PREFERRED EMBODIMENTS

I. Definitions

Figure 1A:
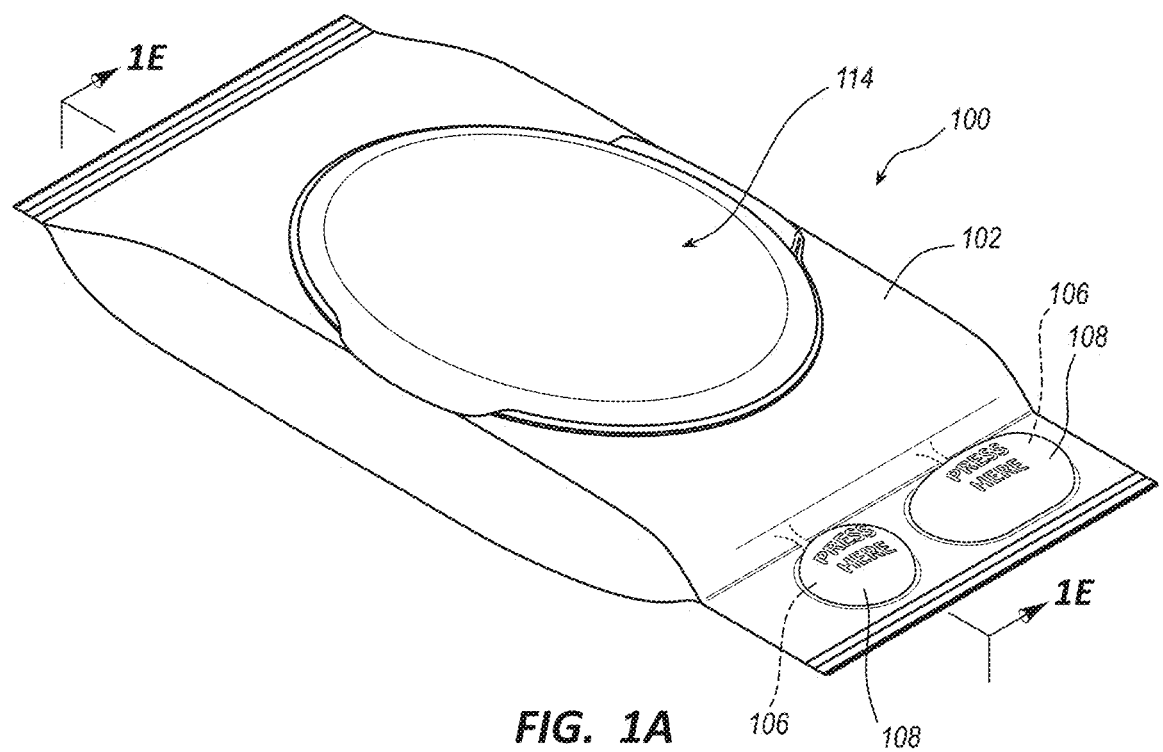
FIGS. 1A-1C show perspective views of an exemplary "flat pack" or "flex pack" system according to an embodiment of the present invention.

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

The term "comprising," which is synonymous with "including," "containing," or "characterized by," is inclusive or open-ended and does not exclude additional, unrecited elements or method steps.

The term "consisting essentially of" limits the scope of a claim to the specified materials or steps "and those that do not materially affect the basic and novel characteristic(s)" of the claimed invention.

The term "consisting of" as used herein, excludes any element, step, or ingredient not specified in the claim.

It must be noted that, as used in this specification and the appended claims, the singular forms "a," "an" and "the" include plural referents unless the content clearly dictates otherwise. Thus, for example, reference to a "surfactant" includes one, two or more such surfactants.

Unless otherwise stated, all percentages, ratios, parts, and amounts used and described herein are by weight.

Numbers, percentages, ratios, or other values stated herein may include that value, and also other values that are about or approximately the stated value, as would be appreciated by one of ordinary skill in the art. As such, all values herein are understood to be modified by the term "about". A stated value should therefore be interpreted broadly enough to encompass values that are at least close enough to the stated value to perform a desired function or achieve a desired result, and/or values that round to the stated value. The stated values include at least the variation to be expected in a typical manufacturing process, and may include values that are within 10%, within 5%, within 1%, etc. of a stated value. Furthermore, where used, the terms "substantially", "similarly", "about" or "approximately" represent an amount or state close to the stated amount or state that still performs a desired function or achieves a desired result. For example, the term "substantially" "about" or "approximately" may refer to an amount that is within 10% of, within 5% of, or within 1% of, a stated amount or value.

Some ranges may be disclosed herein. Additional ranges may be defined between any values disclosed herein as being exemplary of a particular parameter. All such ranges are contemplated and within the scope of the present disclosure.

In the application, effective amounts are generally those amounts listed as the ranges or levels of ingredients in the descriptions, which follow hereto. Unless otherwise stated, amounts listed in percentage ("%'s") are in weight percent (based on 100% active) of any composition.

The phrase 'free of' or similar phrases if used herein means that the composition or article comprises 0% of the stated component, that is, the component has not been intentionally added. However, it will be appreciated that such components may incidentally form thereafter, under some circumstances, or such component may be incidentally present, e.g., as an incidental contaminant.

The phrase 'substantially free of' or similar phrases as used herein means that the composition or article preferably comprises 0% of the stated component, although it will be appreciated that very small concentrations may possibly be present, e.g., through incidental formation, contamination, or even by intentional addition. Such components may be present, if at all, in amounts of less than 1%, less than 0.5%, less than 0.25%, less than 0.1%, less than 0.05%, less than 0.01%, less than 0.005%, less than 0.001%, or less than 0.0001%. In some embodiments, the compositions or articles described herein may be free or substantially free from any specific components not mentioned within this specification.

As used herein, "disposable" is used in its ordinary sense to mean an article that is disposed or discarded after a limited number of usage events, preferably less than 25, more preferably less than about 10, and most preferably after a single usage event. The wipes disclosed herein are typically disposable.

As used herein, the term "substrate" is intended to include any material that is used to clean an article or a surface. Examples of cleaning substrates include, but are not limited to nonwovens, sponges, films and similar materials which in some embodiments can be attached to a cleaning implement, such as a floor mop, handle, or a hand held cleaning tool, such as a toilet cleaning device. In an embodiment, the substrate may be a wipe.

As used herein, "wiping" refers to any shearing action that the wipe undergoes while in contact with a target surface. This includes hand or body motion, substrate-implement motion over a surface, or any perturbation of the substrate via energy sources such as ultrasound, mechanical vibration, electromagnetism, and so forth.

The cleaning compositions dosed onto the substrate as described herein may provide sanitization, disinfection, or sterilization. As used herein, the term "sanitize" shall mean the reduction of "target" contaminants in the inanimate environment to levels considered safe according to public health ordinance, or that reduces a "target" bacterial population by significant numbers where public health requirements have not been established. By way of example, an at least 99% reduction in bacterial population within a 24 hour time period is deemed "significant." Greater levels of reduction (e.g., 99.9%, 99.99%, etc.) are possible, as are faster treatment times (e.g., within 10 minutes, within 5 minutes, within 3 minutes, within 2 minutes, or within 1 minute), when sanitizing. As used herein, the term "disinfect" shall mean the elimination of many or all "target" pathogenic microorganisms on surfaces with the exception of bacterial endospores. As used herein, the term "sterilize" shall mean the complete elimination or destruction of all forms of "target" microbial life and which is authorized under the applicable regulatory laws to make legal claims as a "sterilant" or to have sterilizing properties or qualities. Some embodiments may provide for at least a 2 or more log reduction in a bacterial population within a designated time period (e.g., 10 minutes, 5 minutes, 3 minutes, 1 minute, 30 seconds, 10 seconds or the like). A 2-log reduction is equivalent to a 99% reduction, a 3-log reduction is equivalent to at least a 99.9% reduction, a 4-log reduction is equivalent to at least a 99.99% reduction, a 5-log reduction is equivalent to at least a 99.999% reduction, etc. An example of a target microbe may be *C. diff*. It will be appreciated that microefficacy can also be achieved against other target microbes, numerous examples of which will be apparent to those of skill in the art Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In the application, effective amounts are generally those amounts listed as the ranges or levels of ingredients in the descriptions, which follow hereto. Unless otherwise stated, amounts listed in percentage are in weight percent (based on 100 weight percent active) of the particular material present in the referenced composition, any remaining percentage being water or an aqueous carrier sufficient to account for 100% of the composition, unless otherwise noted. For very low weight percentages, the term "ppm" corresponding to parts per million on a weight/weight basis may be used, noting that 0.1% by weight corresponds to 1000 ppm.

II. Introduction

The present invention relates to systems for sanitization or disinfection, that provide for long term stability of wipes (e.g., nonwoven wipe substrates) provided within a package in an un-dosed condition, in combination with a sanitizing or disinfecting composition also provided within the package, but initially separate from the wipes (e.g., within a burstable pouch, or activated compartment), because upon dosing of the composition onto the wipes, the composition exhibits only relatively short term stability. This configuration of keeping the composition separate from the wipes, but still stored within the as manufactured package, provides convenience to the user, while at the same time providing long term stability for the system as packaged (i.e., wipes and treatment composition separated), while also providing very good surface compatibility (e.g., due to very low bleach concentration) and aesthetic characteristics (e.g., low to negligible bleach odor). At the same time, even though the composition exhibits very low hypochlorite or other free available halide concentration, it advantageously also exhibits very good efficacy against various target microorganisms, such as *C. diff*, *M. bovis*, or the like (e.g., at least a 3-log reduction in such target population within 10 minutes).

Such results are advantageous and even surprising, as it can otherwise be impossible as a practical matter to achieve long-term stability, low bleach odor, and microefficacy, all at the same time.

In addition, Applicant has discovered a surprising relationship between microefficacy and surfactant package selection, particularly for such compositions including only very low levels of hypochlorite or other free available halide oxidant (e.g., less than 1%, less than 0.5%, less than 0.45%, less than 0.4%, or less than 0.35%), as described in Applicant's U.S. application Ser. No. 16/182,415, filed on a Nov. 6, 2018, herein incorporated by reference in its entirety.

The inclusion of less oxidant renders such formulations far more compatible for use on various surfaces, which previously were not routinely treated with hypochlorite containing bleach compositions, out of fear that damage to applied surfaces would result. Similarly, because the concentration of free available chlorine is far lower, such compositions exhibit far less "bleach" odor, making them far more aesthetically appealing for use in healthcare and other environments, where a strong bleach odor can be problematic. For example, previously, a strong bleach composition may have been used in isolation rooms of a hospital or similar setting where a patient infected with *C. diff* may have been kept, which strong composition is effective at sanitizing or disinfecting against such. Nevertheless, because of the low surface compatibility and strong bleach odor such strong composition was not used generally, in other areas of such hospital or similar healthcare facility. As a result, treatments against *C. diff* have largely been reactive, rather than proactive, treating after an infection has already occurred in an individual, rather than a treatment which might be proactive, in preventing infection from occurring in the first place. The present systems and compositions now provide a solution by which healthcare workers or others have a system which can be applied widely and generally, to essentially all surfaces and rooms, and which will be effective against *C. diff* or other target microbes, without the surface compatibility problems, or odor problems associated with previously available solutions.

The present systems address many of such issues, providing systems that ensure long term stability for the system as provided, and which include compositions that include very low levels of hypochlorite or other free available chlorine capable of providing desired microefficacy, and excellent surface compatibility.

III. Exemplary Systems

Figure 1B:
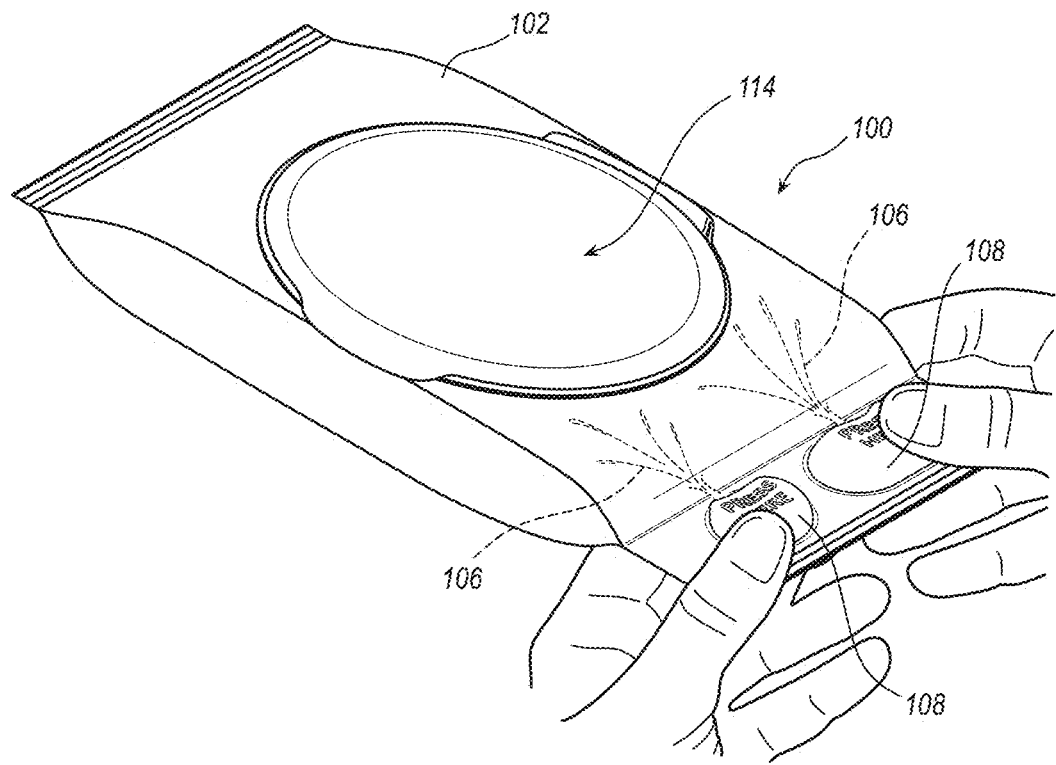
Figure 1C:
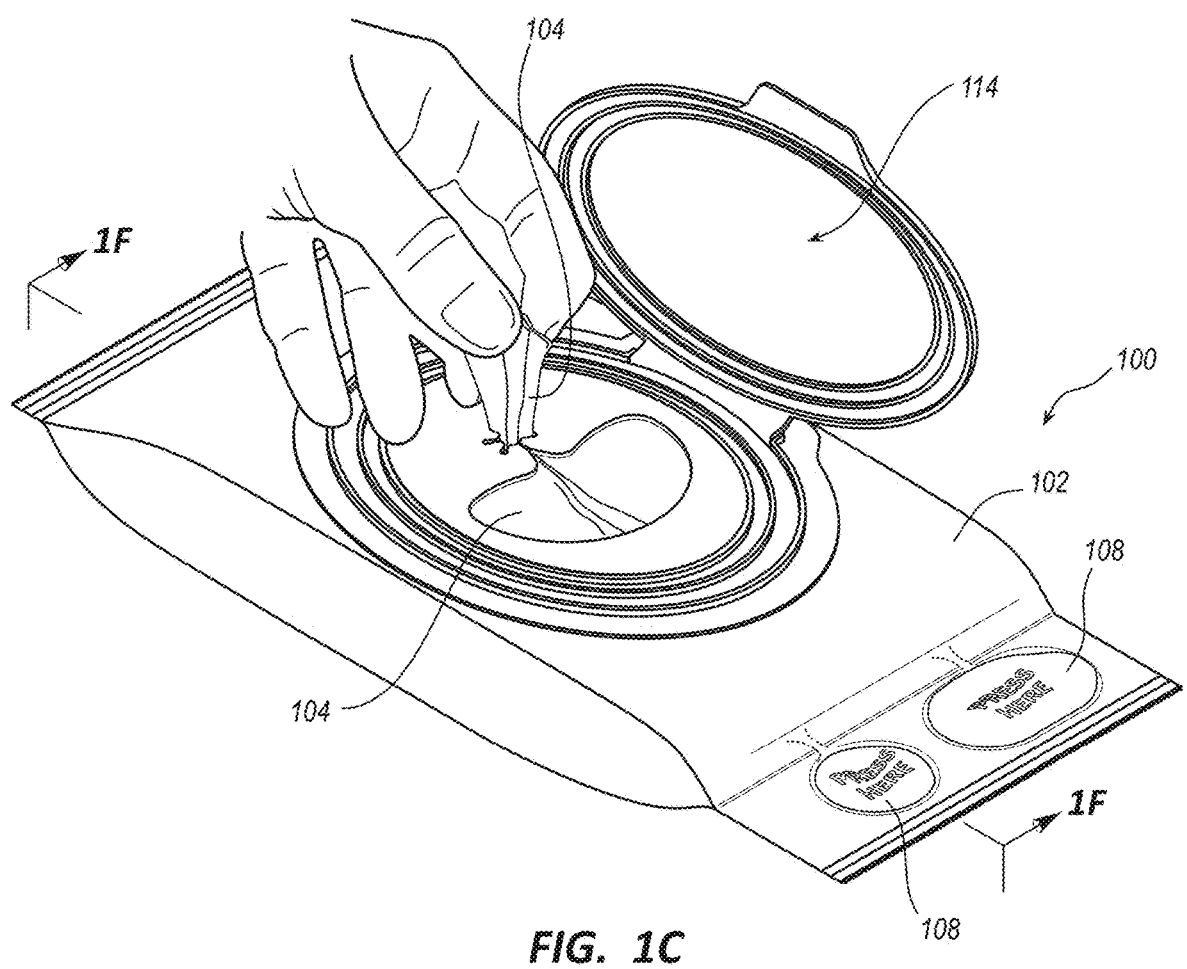

FIGS. 1A-1F illustrate exemplary systems according to various embodiments of the present invention. For example, FIGS. 1A-1C illustrate an exemplary system 100 including a package 102 that contains a plurality of wipes 104 sealed for storage within the package 102. For example, the package 102 may be water-tight, e.g., sealing the wipes within the package. Such water-tight seal becomes important particularly after the initially un-dosed (e.g., dry) wipes are dosed by the user, e.g., immediately prior to initial use, to retain the dosing composition within the package, and keep the wipes from drying out once dosed.

The system 100 further includes a sanitizing or disinfecting composition 106 that is initially stored within a burstable pouch 108 of package 102. The burstable pouch 108 is configured to dose the initially un-dosed (e.g., dry) wipes 104 upon bursting of pouch 108. As noted, the sanitizing or disinfecting composition 106 initially stored within pouch 108 may include a low concentration (e.g., less than 0.5%) of an oxidant, such as a hypochlorite or another free available halide. In addition to low bleach concentration, the composition includes a pH that is less than 12 (e.g., greater than 7, such as 8 to less than 12, such as 11 to 11.5). The composition advantageously provides microefficacy against one or more target microbes (e.g., *C. diff*, *M. bovis*, or the like). For example, in an embodiment, the composition may exhibit at least a 3-log reduction in a *C. diff* population within 10 minutes (e.g., within 5 minutes). Various details of exemplary compositions and exemplary wipe substrates are discussed in more detail below.

a. Free Available Chlorine or Other Halide Oxidant

The compositions advantageously include a component capable of providing a desired relatively low level of free available chlorine or other halide oxidant. While "free available chlorine" and "hypochlorite" are generally used herein when describing the bleach oxidant component, for purposes of simplicity it will be appreciated that a wide variety of other halides can be used, in addition to chlorine oxidizing compounds. For example, analogous compounds based on bromine are often also suitable for use. As such, use of the terms hypochlorite and free available chlorine is meant to encompass analogous hypohalites and similar halide oxidants. Examples of suitable halide oxidants include, but are not limited to alkaline metal salts and/or alkaline earth metal salts of hypochlorous acid, alkaline metal salts and/or alkaline earth metal salts of hypobromous acid, hypochlorous acid, hypobromous acid, solubilized chlorine or other solubilized halide, solubilized chlorine dioxide, acidic sodium chlorite, chlorine-dioxide generating compounds, active chlorine generating compounds, or any other source of free chlorine or other halide oxidant.

Hypohalites refer to salts of hypohalous acids. Hypochlorites and hypochlorous acid may be particularly preferred, although other hypohalites and hypohalous acids (e.g., hypobromites, hypobromous acid, etc.) may also be suitable for use. The salts may be alkali metal or alkaline earth metal salts of a hypohalous acid (e.g., hypochlorous acid), including combinations of salts, or combinations of a salt and an acid. Specific examples of hypohalites include sodium hypochlorite, potassium hypochlorite, calcium hypochlorite, magnesium hypochlorite, lithium hypochlorite, and combinations thereof. Analogous hypobromites and other hypohalites may also be suitable for use.

In an embodiment, the halide oxidant component (broadly referred to herein as hypohalite or other free available halide oxidant) may be present in an amount of about 0.05% to less than 1%, at least 0.1%, at least 0.15%, from 0.1% to less than 0.5% by weight of the composition, from 0.1% to 0.45% by weight of the composition, from 0.1% to 0.4% by weight of the composition, from 0.2% to 0.4% by weight of the composition, or from 0.2% to 0.3% by weight of the composition. In some embodiments, the hypohalite or other free available halide oxidant level may be less than 1%, less than 0.5%, less than 0.4%, or less than 0.35% by weight of the composition. In an embodiment, a concentration greater than 0.5% may be provided (e.g., up to 1%), but in which this higher concentration is intended for dilution, e.g., down to less than 0.5% at time of use.

b. Surfactants

One or more surfactant(s) may be included in the composition. Surfactants have typically been included in bleach compositions to improve the wetting or spreading ability of the formulation on surfaces through a reduction in surface tension, to better solubilize oily soils, or to aid in solubilizing aesthetic components such as fragrances. In the past, the conventional approach has been to formulate such compositions at pH 12 or greater, and to take particular care to select a surfactant that is stable under such extreme pH conditions. As described in Applicant's U.S. application Ser. No. 16/182,415, filed on Nov. 6, 2018, herein incorporated by reference, Applicant has discovered that at low oxidant conditions, surfactant selection may become a major driver to microefficacy of the formulation.

While little attention has previously been paid to any effect that surfactant may have on stability and/or microefficacy, as described in Applicant's U.S. application Ser. No. 16/182,415, the type of surfactant selected for inclusion in the formulation can be very important to achieving the desired stability and/or microefficacy characteristics, particularly at the very low levels of hypochlorite or other free available chlorine as contemplated herein. By way of example, previous compositions employed any surfactant, as selected from various anionic, nonionic, cationic, amphoteric, or zwitterionic surfactants, including mixtures of classes of surfactants, so long as it was stable at the typical high pH value (e.g., 12.5+).

There has been no real development of low-level hypochlorite or other free available chlorine compositions that would exhibit low "bleach" odor, improved surface compatibility, and at the same time provide similar 1-year stability when separated from a wipe used for application, while also exhibiting microefficacy against *C. diff.* or other target microbes. Applicant has discovered that anionic surfactants can have a strong negative effect on stability and/or microefficacy, at the low concentrations of hypochlorite or other free available chlorine as contemplated herein. Nonionic and/or zwitterionic surfactants have been found to have a strong positive effect on stability and/or microefficacy within such low-level bleach formulations. As such, in at least some embodiments, the present compositions advantageously include nonionic and/or zwitterionic surfactants. If included, the concentration of anionic surfactants is limited. At least some embodiments according to the present invention include no anionic surfactants at all. Cationic surfactants may optionally be present. For example, the composition may have an R value that is greater than 0 (e.g., 0.5 or more, such as equal to 1) where R is defined as the sum of the concentration of any nonionic and/or zwitterionic surfactants, plus any included cationic surfactants, divided by total surfactant concentration.

Examples of nonionic surfactants include, but are not limited to, alcohol ethoxylates, alcohol propoxylates, alkyl phosphine oxides, alkyl glucosides and alkyl pentosides, alkyl glycerol esters, alkyl ethoxylates, and alkyl and alkyl phenol ethoxylates of all types, poly alkoxylated (e.g. ethoxylated or propoxylated) $C_6$-$C_{12}$ linear or branched alkyl phenols, $C_6$-$C_{22}$ linear or branched aliphatic primary or secondary alcohols, and $C_2$-$C_5$ linear or branched aliphatic glycols. Block or random copolymers of $C_2$-$C_6$ linear or branched alkylene oxides may also be suitable nonionic surfactants. Capped nonionic surfactants in which the terminal hydroxyl group is replaced by halide; $C_1$-$C_8$ linear, branched or cyclic aliphatic ether; $C_1$-$C_8$ linear, branched or cyclic aliphatic ester; phenyl, benzyl or $C_1$-$C_4$ alkyl aryl ether; or phenyl, benzyl or $C_1$-$C_4$ alkyl aryl ester may also be used. Sorbitan esters and ethoxylated sorbitan esters may also be useful nonionic surfactants. Other suitable nonionic surfactants may include mono or polyalkoxylated amides of the formula $R^1CONR^2R^3$ and amines of the formula $R^1NR^2R^3$ wherein $R^1$ is a $C_5$-$C_{31}$ linear or branched alkyl group and $R^2$ and $R^3$ are $C_1$-$C_4$ alkyl, $C_1$-$C_4$ hydroxyalkyl, or alkoxylated with 1-3 moles of linear or branched alkylene oxides. Biosoft 91-6 (Stepan Co.) is an example of an alkyl ethoxylate (or alcohol ethoxylate) having a methylene chain length of $C_9$ to $C_{11}$ with an average of 6 moles of ethoxylation. An example of an alcohol ethoxylate is ECOSURF EH-9, which is more specifically an ethylene oxide-propylene oxide copolymer mono(2-ethylhexyl) ether, available from Sigma-Aldrich.

Alkylpolysaccharides that may be suitable for use herein are disclosed in U.S. Pat. No. 4,565,647 to Llenado, having a linear or branched alkyl, alkylphenyl, hydroxyalkyl, or hydroxyalkylphenyl group containing from 6 to 30 carbon atoms and a polysaccharide, e.g., a polyglycoside, hydrophilic group containing from 1.3 to 10 saccharide units. Suitable saccharides include, but are not limited to, glucosides, galactosides, lactosides, and fructosides. Alkylpolyglycosides may have the formula: $R^2O(CnH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 10.

Fatty acid saccharide esters and alkoxylated fatty acid saccharide esters may also be suitable for use in the present invention. Examples include, but are not limited to, sucrose esters, such as sucrose cocoate, and sorbitan esters, such as polyoxyethylene(20) sorbitan monooleate and polyoxyethylene(20) sorbitan monolaurate.

Phosphate ester surfactants may also be suitable. These include mono, di, and tri esters of phosphoric acid with $C_4$-$C_{18}$ alkyl, aryl, alkylaryl, alkyl ether, aryl ether and alkylaryl ether alcohols (e.g. disodium octyl phosphate).

Zwitterionic surfactants may be employed. Many such zwitterionic surfactants contain nitrogen. Examples of such include amine oxides, sarcosinates, taurates and betaines. Examples include $C_8$-$C_{18}$ alkyldimethyl amine oxides (e.g., octyldimethylamine oxide, lauryldimethylamine oxide (also known as lauramine oxide), and cetyldimethylamine oxide), $C_4$-$C_{16}$ dialkylmethylamine oxides (e.g. didecylmethylamine oxide), $C_8$-$C_{18}$ alkyl morpholine oxide (e.g. laurylmorpholine oxide), tetra-alkyl diamine dioxides (e.g. tetramethyl hexanane diamine dioxide, lauryl trimethyl propane diamine dioxide), $C_8$-$C_{18}$ alkyl betaines (e.g. decylbetaine and cetylbetaine), $C_8$-$C_{18}$ acyl sarcosinates (e.g. sodium lauroylsarcosinate), $C_8$-$C_{18}$ acyl $C_1$-$C_6$ alkyl taurates (e.g. sodium cocoylmethyltaurate), $C_8$-$C_{18}$ alkyliminodipropionates (e.g. sodium lauryliminodipropionate), and combinations thereof. Lauryl dimethyl amine oxide (Ammonyx LO) myristyl dimethyl amine oxide (Ammonyx MO), decylamine oxide (Ammonyx DO) are examples of suitable zwitterionic surfactants, available from Stepan Co.

Cationic surfactants may optionally be included, e.g., in combination with a nonionic and/or zwitterionic surfactant. Examples of cationic surfactants include, but are not limited to monomeric quaternary ammonium compounds, monomeric biguanide compounds, and combinations thereof.

Suitable exemplary quaternary ammonium compounds are available from Stepan Co. under the tradename BTC (e.g., BTC 1010, BTC 1210, BTC 818, BTC 8358). Any other suitable monomeric quaternary ammonium compound may also be employed. BTC 1010 and BTC 1210 are described as didecyl dimethyl ammonium chloride and a mixture didecyl dimethyl ammonium chloride and n-alkyl dimethyl benzyl ammonium chloride, respectively. Examples of monomeric biguanide compounds include, but are not limited to chlorhexidine, alexidine and salts thereof. Cetyl ($C_{16}$) trimethylammonium chloride (CETAC) and pentyl ($C_5$) trimethyl ammonium chloride are specific examples of cationic quaternary ammonium surfactants. Quaternary ammonium compounds are described in more detail in U.S. Pat. No. 6,825,158, incorporated by reference herein, and will already be familiar to those of skill in the art.

Additional exemplary cationic surfactants include alkyltrimethylammonium, alkylpryidinium, and alkylethylmorpholinium salts, in which the alkyl group contains 4 to 18 carbon atoms, alternatively 12 to 16 carbon atoms. The alkyl chains may be linear or branched or contain an aryl group. The counterion may be, but is not limited to, chloride, sulfate, methylsulfate, ethylsulfate, or toluene sulfonate. Other suitable cationic surfactants include dialkyldimethyl ammonium salts, in which the alkyl groups each contain 4 to 12 carbon atoms such as dioctyldimethyl ammonium chloride. Other suitable cationic surfactants may have two quaternary ammonium groups connected by a short alkyl chain such as N-alkylpentamethyl propane diammonium chloride. In the above cationic surfactants the methyl substituents can be completely or partially replaced by other alkyl or aryl substituents such as ethyl, propyl, butyl, benzyl, and ethylbenzyl groups, for example octyldimethylbenzyl ammonium chloride and tetrabutylammonium chloride.

In one embodiment, the present formulations may avoid the use of anionic surfactants. Non-limiting examples of such anionic surfactants that may be excluded include: alkyl sulfates (e.g., $C_8$-$C_{18}$ linear or branched alkyl sulfates such as sodium lauryl sulfate (SLS), and sodium tetradecylsulfate), alkyl sulfonates (e.g., $C_6$-$C_{18}$ linear or branched alkyl sulfonates such as sodium octane sulfonate and sodium secondary alkane sulfonate, alkyl ethoxysulfates, fatty acids and fatty acid salts (e.g., $C_6$-$C_{16}$ fatty acid soaps such as sodium laurate), and alkyl amino acid derivatives. Other examples that may be excluded include: sulfate derivatives of alkyl ethoxylate propoxylates, alkyl ethoxylate sulfates, alpha olefin sulfonates, $C_6$-$C_{16}$ acyl isethionates (e.g. sodium cocoyl isethionate), $C_6$-$C_{18}$ alkyl, aryl, or alkylaryl ether sulfates, $C_6$-$C_{18}$ alkyl, aryl, or alkylaryl ether methylsulfonates, $C_6$-$C_{18}$ alkyl, aryl, or alkylaryl ether carboxylates, sulfonated alkyldiphenyloxides (e.g. sodium dodecyldiphenyloxide disulfonate), and the like.

Additional examples of suitable nonionic and/or zwitterionic surfactants include lauryl dimethyl amine oxide (Ammonyx LO), also known as lauramine oxide, myristyl dimethyl amine oxide (Ammonyx MO), decylamine oxide (Ammonyx DO), other amine oxides, any betaines, linear alcohol ethoxylates, alcohol propoxylates, alkyl polyglucosides, and combinations thereof. Cationic surfactants, such as any quaternary ammonium chloride may optionally be present.

In one embodiment, examples of anionic surfactants that may be excluded include: sodium lauryl sulfate (SLS), linear alkylbenzene sulfonate (LAS), any other sulfates, sulfonates, disulfonates, and any carboxylate fatty acids, particularly where such include alkyl groups have more than 1, more than 2, more than 3, more than 4, or 8 or more carbon atoms in the alkyl group.

In an alternative embodiment of the invention, a anionic surfactant may be included as surfactant aid. An example of such a suitable surfactant aid is an aromatic sulfonate, such as sodium xylene sulfonate ("SXS") or sodium lauryl sulfate (SLS). Other aromatic sulfonates may similarly serve as acceptable surfactant aids, particularly where they have no alkyl groups larger than a methyl group (e.g., sodium mesitylene sulfonate "SMS", or the like).

In one embodiment, the surfactants may be selected based on green or natural criteria. For example, there is an increasing desire to employ components that are naturally-derived, naturally-processed, and biodegradable, rather than simply being recognized as safe. Such "natural surfactants" may be produced using processes perceived to be more natural or ecological, such as distillation, condensation, extraction, steam distillation, pressure cooking and hydrolysis.

Additional examples of various surfactants are given in U.S. Pat. No. 3,929,678 to Laughlin and Heuring, U.S. Pat. No. 4,259,217 to Murphy, and U.S. Publication No. 2013/0028990. The above patents and applications are each herein incorporated by reference in their entirety.

In one embodiment, the formulation may have an R value, where R is the sum of the concentration of any "good" surfactants (e.g., nonionic, zwitterionic, and cationic surfactants) divided by total surfactant concentration (including surfactant aids). Such R value may be greater than 0, such as from 0.01 to 1, from 0.1 to 1, from 0.5 to 1, greater than 0.3, greater than 0.35, greater than 0.4, greater than 0.45, greater than 0.5, greater than 0.55, greater than 0.6, greater than 0.65, greater than 0.7, greater than 0.75, greater than 0.8, greater than 0.9, or equal to 1 (i.e., all surfactants included are "good", with no anionic surfactants or surfactant aids included). In an embodiment, the value of R may be equal to 1, but for the inclusion of a surfactant aid (such as SXS). As described herein, while SXS technically decreases the R value, the practical effect of its inclusion does not negate the microefficacy and/or stability benefits associated with otherwise high R values. In other words, a composition that includes an R value that is less than 1 (e.g., 0.5) solely because of the inclusion of an anionic surfactant aid exhibits far better microefficacy and/or stability as compared to a similar composition of the same R value, but where the decrease in R value is because of the inclusion of an anionic surfactant having a long alkyl group, such as SLS.

In another embodiment, the R values may also refer to the "best" nonionic and/or zwitterionic surfactants, absent any "acceptable" cationic surfactants that may be included. For example, while cationic surfactants may be acceptable, they are typically used in combination with a nonionic and/or zwitterionic surfactant. As such, the total of nonionic and/or zwitterionic surfactants may account for at least 30%, at least 35%, at least 40%, at least 45%, at least 50%, at least 55%, at least 60%, at least 65%, at least 70%, at least 75%, at least 80%, at least 85%, or at least 90% of total surfactants.

In an embodiment, surfactant concentration may typically be far lower than many other bleach formulations, e.g., given the low level of other active ingredients in the formulation. For example, total surfactant concentration may range from 0.001% by weight to 1% by weight, from 0.01% to 0.5% by weight, from 0.01% by weight to 0.1% by weight. The ratio of surfactant to hypohalite or other free available halide oxidant may be from 1:1 to 100:1, from 3:1 to 50:1, from 5:1 to 20:1 or from 5:1 to 15:1.

The composition may have a low viscosity, e.g., such as up to 1000 cps, or 1 to 100 cps.

c. Other Adjuvants

In addition to the oxidant and any optional surfactant(s), a wide range of optional adjuvants may be present. For example, buffers, oils, fragrances, solvents, pH adjusters (e.g., acids or bases), builders, silicates, preservatives and chelating agents, including but not limited to EDTA salts, GLDA, gluconates, 2-hydroxyacids and derivatives, glutamic acid and derivatives, trimethylglycine, etc. may be included.

Dyes and colorants may be present. Thickeners may be present.

Enzymes may be present in some embodiments.

Water-miscible solvents may be present in some embodiments. Lower $C_1$-$C_4$ alcohols (e.g., ethanol, t-butanol), ethylene glycol, propylene glycol, glycol ethers, and mixtures thereof with water miscibility at 25° C. may be present in some embodiments. Other embodiments may include no lower alcohol (e.g., particularly ethanol or methanol) or glycol ether solvents. Where such solvents are present, some embodiments may include them in only small amounts, for example, of not more than 5%, not more than 3%, not more than 2%, not more than 1%, or not more than 0.5% (e.g., from 0.01% to 0.5%) by weight.

Water-immiscible oils or solvents may be present, e.g., being solubilized into surfactant micelles. Among these oils include those added as fragrances. Preferred oils are those that are from naturally derived sources, including the wide variety of so-called essential oils derived from a variety of botanical sources. Formulations intended to provide antimicrobial benefits, coupled with improved overall sustainability may advantageously comprise quaternary ammonium compounds and/or monomeric biguanides such as water soluble salts of chlorhexidine or alexidine in combination with essential oils such as thymol and the like, preferably in the absence of water-miscible alcohols.

Silicates, builders, chelating agents, preservatives, fragrances, and any other adjuvants may be included in appropriate, effective amounts. In some embodiments, such levels may be from 0.01 to 10% by weight, or from 0.1 to 5% by weight, or from 0.1 to 1% by weight.

Suitable buffers include those materials capable of controlling ultimate solution pH and which themselves resist reaction with the oxidant and remain in sufficient concentration to control the pH. Suitable buffers further include those buffers that are non-consumable with respect to action by the hypochlorite or other free available chlorine oxidant. In addition, suitable buffers may have an acid dissociation constant (Ka) at 20° C. in the range from $1\times10^{-2}$ to $1\times10^{12}$, from $1\times10^{-3}$ to $1\times10^{11}$, from $1\times10^{-3}$ to $1\times10^{-8}$, or from $1\times10^{-8}$ to $1\times10^{12}$.

Suitable buffers may include salts and/or corresponding conjugate acids and bases of the following classes of materials, and their derivatives: carbonates, bicarbonates, silicates, boric acid and borates, di- and mono-basic phosphates or phosphoric acid, monocarboxylic or polycarboxylic acids such as acetic acid, succinic acid, octanoic acid, the like, and combinations thereof. Sodium carbonate is one such specific example.

N-sodium silicate, which serves to protect metal surfaces from damage, may be present. Other silicate salts or phosphate salts may alternatively be used for such. Such silicates or phosphates may be present in a range of up to 0.2%, up to 0.1%, or up to 0.05% by weight. Such low concentrations are preferred to minimize build-up on any treated surfaces. The compositions may provide low residue characteristics, as described below in conjunction with FIGS. 5A-5B.

In an embodiment, the buffer, if present, may be present from 0.001% by weight to 10% by weight, from 0.01% to 5% by weight, from 0.1% by weight to 1% by weight, or from 0.1% to 0.5% by weight.

Various other components that may be included in at least some compositions provided separate, for dosing by the user immediately prior to use, may be disclosed in U.S. Pat. Nos. 6,825,158; 8,648,027; 9,006,165; 9,234,165, and U.S. Publication No. 2008/003906 each of which is herein incorporated by reference in its entirety. In an embodiment, it may even be possible to provide one or more of the actives of the composition (e.g., powdered hypohalite, surfactant, quats, silver (e.g., for silver ion antimicrobial effect), activators, etc. in dry form, where the pouch is filled with water, which upon release forms the desired sanitizing or disinfecting composition, dosed on the wipe.

pH values for the present compositions may be about 7 to 12.5, about 8 to 11.9, and less than 12.5, such as 8 to less than 12, greater than 9, 10 or greater, about 9 to 11.9, about 10 to 11.5 or less, such as 11 to 11.5, or the like. The relatively lower pH somewhat increases the variety of organic surfactants that can be used, as stable under such conditions. It also increases microefficacy, particularly where the oxidant concentration is already so low.

The compositions are liquids. The vast majority of the composition may comprise water (e.g., at least 90%, at least 95%, at least 97%, at least 98%, or at least 99% water).

Compositions including low levels of hypochlorite or other free available chlorine as described herein may be used in a wide variety of environments where sanitization and/or disinfection is desired. Examples of such include but are not limited to cleaning, disinfection, sterilization, deodorization, mold removal, toxin and/or allergen remediation, application to surfaces that may contact food, treatment of hard surfaces, fabrics or other soft surfaces, treatment of tools or other implements in health care or other settings, glass cleaners, toilet cleaning, and the like. The compositions may be provided as a ready-to-use liquid, included in a burstable pouch of a package that also includes a plurality of wipes which are initially undosed, and upon activation (e.g., bursting) of the pouch, the composition is released for absorption into the wipes, e.g., as illustrated in FIG. 1B.

For example, FIG. 1A shows how the package 102 may include one or more pouches 108 that may be configured to store the composition long term, in a stable condition (e.g., for up to 6 months, or up to 1 year), with minimal reduction in hypochlorite or other free halide concentration during such relatively long shelf-life. The pouch 108 may be configured as a "bubble" or other structure that is specifically engineered to deliver the composition into that portion of the package containing the wipes, when the "bubble" is burst, releasing the composition from the pouch (but still retained within the package 102). For example, as shown in FIG. 1E-1F, the pouch 108 may be separated from that portion of the interior of the package or other container 102 that houses the wipes 104 in a sealed internal cavity 110. In an embodiment, such initial separation may be provided by a burstable membrane 112, e.g., which irreversibly ruptures upon application of sufficient pressure on the exterior of pouch 108 (e.g., compressing composition 106 against membrane 112). Such a burstable membrane may simply be a region of material separating the chamber 107 in which composition 106 is stored, from chamber 110, in which the initially undosed wipes 104 are stored, as shown in FIG. 1E. Such membrane may be thinner (e.g., weaker) than any surrounding boundary material, to ensure rupture occurs through such membrane. In an embodiment, the membrane (and all boundary material defining the interior cavity of pouch 108) may be formed from a material that is non-reactive with hypochlorite compositions, such as polyethylene. For example, package 102 may similarly be formed from polyethylene. FIG. 1E shows such a membrane intact, before bursting, while FIG. 1F shows the configuration after bursting has occurred, and the composition has been forced out of pouch 108, into chamber 110, dosing wipes 104. While one such configuration is shown, it will be appreciated that numerous alternatives are possible for providing initial separation of the composition 106, still within the same package in which wipes 104 are also stored, which allows dosing of the wipes just before initial use of one or more of such wipes. For example, instead of an irreversibly burstable membrane, a valve (e.g., a one-way valve) could be employed, to provide similar results.

While in an embodiment the wipes stored within portion 110 may be substantially dry, in another embodiment, it is possible that they will be pre-wetted with a liquid composition (e.g., simply water), or dry-loaded (e.g. loaded with surfactant or other actives but substantially dry) and they become dosed with the composition including the hypochlorite or other halide oxidant at the time of activation of pouch 108. In any case, the wipes 104 are not loaded or dosed with the liquid treatment composition as described herein, including a low concentration of such a hypochlorite or the like until just before use.

Package 102 may include any of variously configured re-sealable closures, e.g., such as any of various rigid closures, such as exemplary rigid closure 114 illustrated in FIGS. 1A-1C. It will be apparent that numerous other closures and package configurations are also possible. For example, the closure could be flexible in nature (e.g., a flap that reseals over the opening in the package, through which wipes are pulled). While the package 102 is shown as a "flex pack", it will be apparent that numerous other possible packaging configurations are also possible, e.g., such as a tub (e.g., with a lid having a re-sealable opening through the lid), a canister (e.g., in which the wipes are configured as a "donut" that stands vertically within such a cylindrical canister, as in FIG. 1G), or the like. For example, FIG. 1G shows a system 200, with a vertical canister 202, where wipes 104 are provided as a "donut", standing vertically within canister 202. Such canister includes initially sealed pouch(es) 208, containing the sanitizing or disinfecting composition 106, for release and dosing of wipes 104 by the user, immediately prior to use.

It will be apparent that the specifics of the packaging, and the arrangement of the wipes therein (e.g., as a stack of wipes where the wipes are arranged horizontally, in a planar stack as represented in 1E-1F, as a donut in a canister, as in FIG. 1G, etc.) are not particularly limited, and any of various possibilities may be suitable for use with the systems described herein. Additional re-sealable containers and dispensers that may be adapted for use as described herein (e.g., to include a burstable pouch with the sanitizing or disinfecting composition initially stored separately therein) include, but are not limited to, those described in U.S. Pat. No. 4,171,047 to Doyle et al., U.S. Pat. No. 4,353,480 to McFadyen, U.S. Pat. No. 4,778,048 to Kaspar et al., U.S. Pat. No. 4,741,944 to Jackson et al., U.S. Pat. No. 5,595,786 to McBride et al.; the entire contents of each of the aforesaid references are incorporated herein by reference. It will be appreciated that numerous other possible containers could be used.

Typically, the wipes 104 are stacked or rolled and placed in the container during mass manufacturing, without dosing them. Various examples of interleaving and/or stacking configurations that may be used in a "flat pack", "flex pack" or tub like container configuration are shown in U.S. Publication 2016/0031632, herein incorporated by reference in its entirety.

In any case, the package may provide a water-tight, as well as an air-tight seal. For example, the water-tight seal can prevent or minimize drying out of the wipes once the pouch has been activated, dosing the wipes. An air-tight seal may minimize dissolution of $CO_2$ from the atmosphere into the solution (either before or after activation), which $CO_2$ can otherwise result in formation of carbonic acid, undesirably dropping the pH (affecting stability).

Figure 1D:
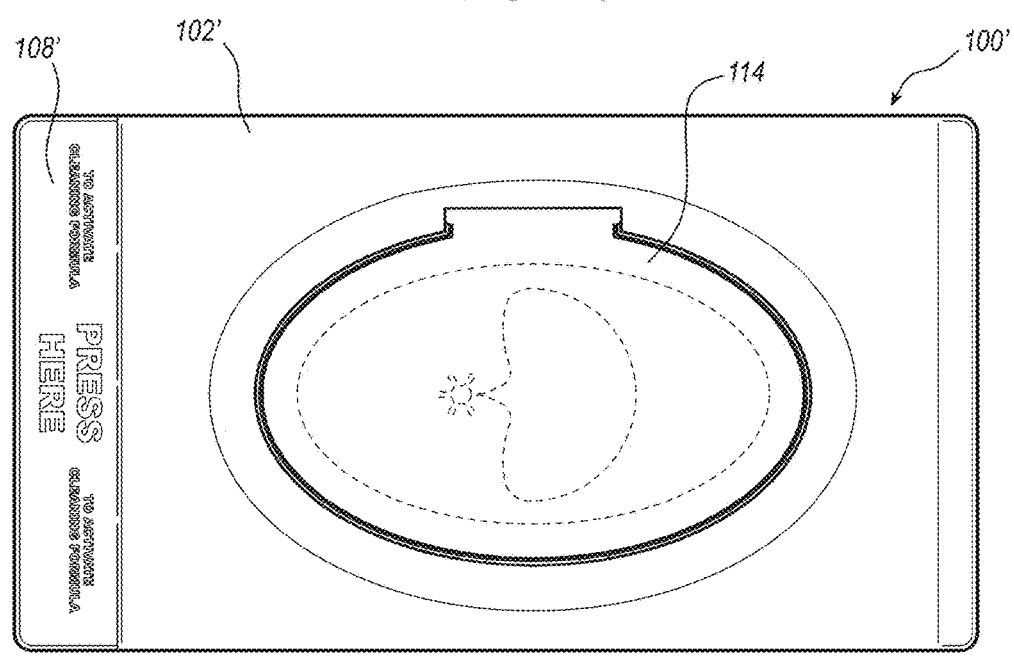
FIG. 1D illustrates another exemplary system according to another embodiment.
Figure 1G:
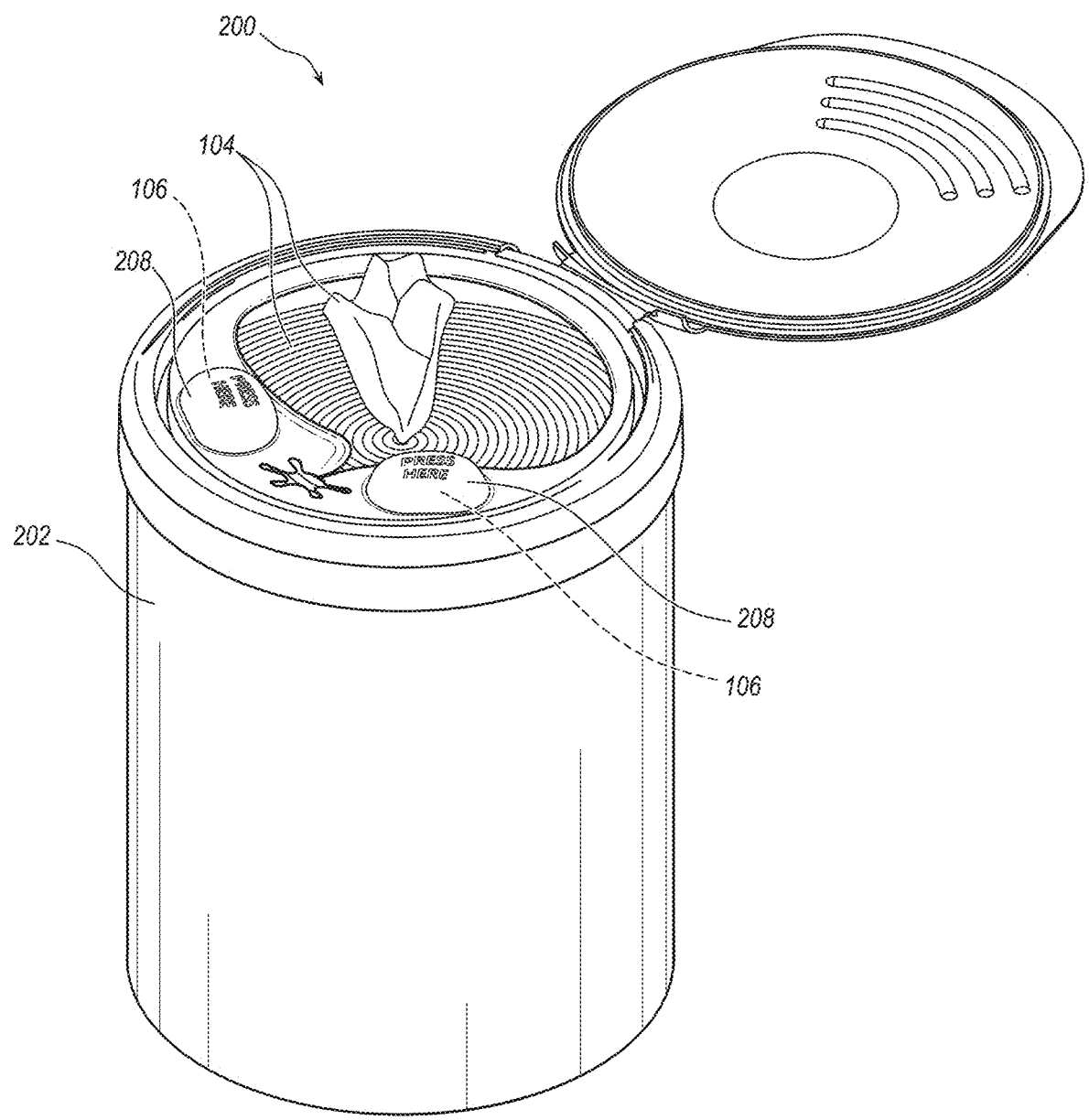
FIG. 1G shows an alternative exemplary system in which the container or package is configured as a cylinder, in which the wipes are configured as a "donut" that is received into the cylinder.

While FIGS. 1A-1C and 1E-1F illustrate an embodiment that may include a plurality of pouches 108 initially holding the sanitizing or disinfecting composition 106, FIG. 1D illustrates another embodiment of a system 100' and package 102' that may be similarly configured to those of FIGS. 1A-1C, but which is shown as including a single pouch 108' (e.g., at an end of package 100'), that may be filled with the composition 106. It will be apparent that numerous configurations for the package, and placement of the burstable pouch 108' are possible. While FIGS. 1A-1C show two pouches 108, on the same side of package 102, it will be apparent that where there are multiple pouches 108, they could be positioned on different sides, e.g., to better equilibrate dosing of the composition 106 into wipes 104.

d. Wipes

The wipe may be formed from a material that comprises synthetic or non-synthetic (e.g., pulp) fibers, a blend of pulp and synthetic fibers, or just pulp fibers. The wipe may be a nonwoven. Any of various nonwoven materials may be used, which are widely available from various commercial sources. Such layers and fibers may be wetlaid, airlaid, meltblown, spunbond, spunlaid, SMS (spunbond-meltblown-spunbond), coform, carded webs, thermal bonded, thermoformed, spunlace, hydroentangled, needled, or chemically bonded. In an embodiment, such surface layers may also incorporate a fraction of pulp fibers therein (e.g., as a homogenous blend of randomly distributed synthetic and pulp fibers, or where the pulp fibers are positioned non-randomly, e.g., at an exterior, or at an interior surface). In an embodiment, substantially all of the fibers in the wipe may be synthetic fibers. In another embodiment, some fraction of the fibers, even up to 100% thereof, may comprise pulp fibers. In one embodiment, the wipes may be compostable. Alternatively, blends of pulp and synthetic fibers can be used, as those of ordinary skill in the art will appreciate.

A wide variety of synthetic materials that can be formed into fibers, and laid into a nonwoven substrate layer are appropriate for use in the contemplated multi-layer substrates. Examples of such polymeric synthetic materials include, but are not limited to polyethylene, polypropylene, PET, PVC, polyacrylics, polyvinyl acetates, polyvinyl alcohols, polyamides, polystyrenes, or the like. No matter the choice of materials (e.g., pulp or synthetic), the wipe may have a basis weight of 30-120 gsm, such as 30-80 gsm.

Additional details of various possible suitable substrates, including nonwoven substrates are found in U.S. Publication No. 2005/0155630, as well as U.S. application Ser. No. 16/036,095, filed on Jul. 16, 2018, U.S. application Ser. No. 16/036,688, filed on Jul. 16, 2018, and U.S. application Ser. No. 16/042,690, filed on Jul. 23, 2018, respectively, each of which is herein incorporated by reference in its entirety. The wipes can be formed by any of a number of different techniques, as will be apparent to those of skill in the art.

IV. Examples

Exemplary sanitizing and disinfecting compositions that are formulated to include a low concentration of hypochlorite are shown below in Table 1. Those with R values greater than 0, may be advantageous, for reasons described above. Microefficacy of such compositions against *C. diff* and TB (e.g., *Mycobacterium Bovis*) was tested, as described in Applicant's U.S. application Ser. No. 16/182,415, already incorporated by reference in its entirety.

TABLE 1

| Sample | NaOCl (ppm) | SLS (wt %) | LO (wt %) | SXS (wt %) | t-butanol (wt %) | silicate (wt %) | pH | Calculated R value |
|---|---|---|---|---|---|---|---|---|
| A | 2000 | — | 0.05 | 0.1 | 0.5 | — | 10.5 | 0.33 |
| B | 2000 | — | 0.05 | 0.1 | 0.1 | — | 10.5 | 0.33 |
| C | 2000 | 0.05 | — | — | 0.1 | — | 10.5 | 0 |
| D | 2000 | 0.05 | — | — | 0.5 | — | 10.5 | 0 |
| E | 3000 | 0.05 | — | 0.033 | — | — | 11 | 0 |
| F | 2000 | — | — | — | — | — | 10 | — |
| G | 2000 | 0.05 | — | — | — | — | 10 | 0 |
| H | 2000 | — | — | — | — | — | 11.6 | 0 |
| I | 2000 | 0.05 | — | — | — | — | 11.6 | 0 |
| J | 2000 | — | 0.03 | — | — | — | 10.5 | 1 |
| K | 2000 | — | 0.03 | — | 0.1 | — | 10.5 | 1 |
| L | 2000 | 0.03 | — | — | 0.1 | — | 10.5 | 0 |
| M | 2500 | — | 0.03 | — | — | — | 11 | 1 |
| N | 2500 | — | 0.03 | — | 0.1 | — | 11 | 1 |
| O | 2500 | 0.03 | — | — | — | — | 11 | 0 |
| P | 2000 | — | 0.05 | 0.1 | 0.1 | 0.25 | 10 | 0.33 |
| Q | 2000 | — | 0.05 | 0.1 | 0.1 | 0.25 | 10.5 | 0.33 |
| R | 2500 | — | 0.05 | 0.1 | 0.1 | 0.25 | 10.5 | 0.33 |
| S | 2500 | — | 0.05 | 0.1 | — | 0.25 | 10.5 | 0.33 |
| T | 2000 | — | 0.1 | 0.1 | 0.1 | 0.25 | 11 | 0.5 |
| U | 2500 | — | 0.05 | 0.1 | — | 0.25 | 11 | 0.33 |
| V | 2000 | — | 0.03 | — | — | 0.25 | 10.6 | 1 |
| W | 2500 | — | 0.03 | — | — | 0.25 | 10.6 | 1 |
| X | 2000 | — | 0.05 | 0.04 | — | 0.25 | 10.6 | 0.56 |

LO = lauryl dimethyl amine oxide (Ammonyx LO)
SLS = sodium lauryl sulfate
SXS = sodium xylene sulfonate Examples V and W exhibited particularly good phase stability, shelf stability, and effectivity against both *C. diff* and TB, at very low hypochlorite (e.g., free available chlorine) concentrations. Examples M, N and T also exhibited promising results.

Figure 2:
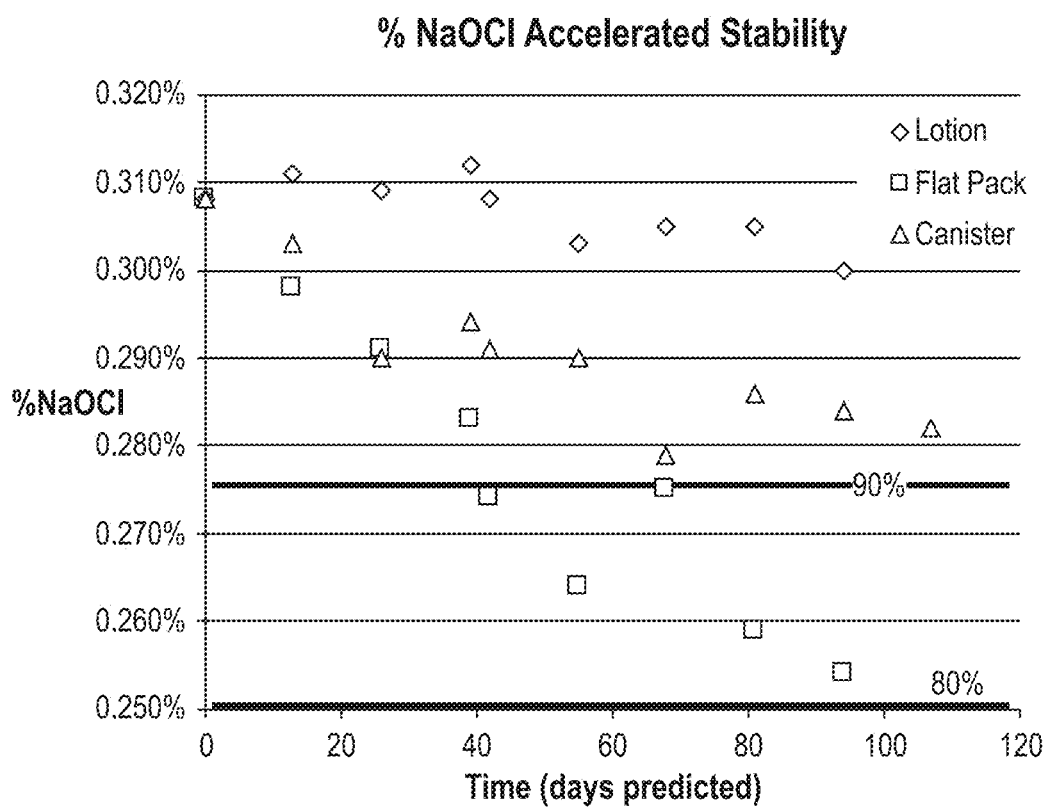
FIGS. 2-3 show stability results for an exemplary composition for use in the present systems, both alone (not dosed on a wipe) and dosed on differently packaged synthetic wipes (flat pack and canister).
Figure 3:
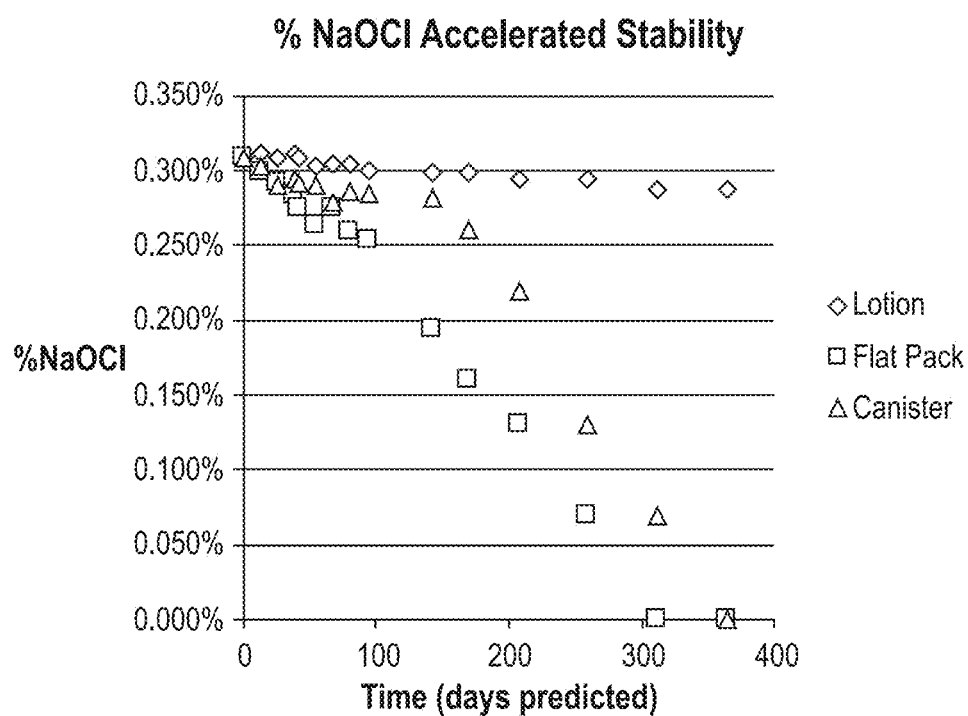

FIGS. 2-3 illustrate stability results for an exemplary bleach composition similar to those shown in Table 1 (e.g., with a low initial hypochlorite concentration of about 2500 to 3100 ppm, a pH of 11.2, 30 ppm of Ammonyx LO, 3000 ppm of a buffer, and 660 ppm of a silicate), shown for the composition or "lotion" alone (not dosed on any substrate), as well as for the same composition dosed on wipes in a flat pack (e.g., similar to a configuration such as that shown in FIG. 1F), and for the same composition and same wipes, but where the wipes are configured as a "donut" packaged within a canister (e.g., as in FIG. 1G). The wipes used for the test were substantially fully synthetic wipes (e.g., PET), with substantially no pulp content, having a weight basis of 52 gsm.

Such accelerated stability testing is routinely performed at an elevated temperature (e.g., 120° F.) on an accelerated time schedule to predict shelf-stability. For example, 28 days at 120° F. may be indicative of 1 year stability at 70° F. Details of such accelerated stability testing are disclosed in Applicant's U.S. Pat. Nos. 7,008,600 and 7,070,737, each of which is herein incorporated by reference in its entirety. The results show that the composition alone (e.g., as stored within pouch 108) exhibits stability, for example, exhibiting no more than a maximum threshold drop (e.g., 10%, 20%, 25%, or 30%) in hypochlorite concentration for 1 year. The results also show that when dosed on the substrate, stability may be provided for perhaps 90-180 days, depending on the threshold of the drop in hypochlorite concentration that is acceptable. FIGS. 2 and 3 also interestingly show that packaging the wipes as a donut within a canister may provide for better overall stability as compared to packaging within a "flat pack", all else being equal.

With respect to chlorine concentration, chlorine may be routinely measured and/or reported as free available chlorine, combined chlorine, or total residual chlorine. Free available chlorine refers to generally 3 forms of chlorine that may be found in such formulations: (a) elemental chlorine ($Cl_2$), (b) hypochlorous acid (HOCl), and (c) hypochlorite ion (OCl). As used herein, use of the phrase "free available chlorine" for practical purposes may be the same as the hypochlorite concentration, as while some hypochlorous acid and/or dissolved $Cl_2$ may be present, the hypochlorite represents the vast majority of such free available chlorine, and it is typically a concentration or amount of hypochlorite that is added to the formulation (after which some of this forms hypochlorous acid and/or dissolved $Cl_2$) according to equilibrium. In other words, if 2500 ppm of hypochlorite is initially added to a given formulation, the free available chlorine may also be 2500 ppm. The vast majority of that amount may remain as hypochlorite, while some small fraction thereof may be converted to hypochlorous acid and/or dissolved $Cl_2$, but the formulation would continue to initially exhibit a free available chlorine concentration of 2500 ppm. Over time or during use, such components are consumed as an oxidant, in reaction, or decomposition of such components gradually occurs, reducing the free available chlorine concentration. As described above, other halides (e.g., bromine) can be understood as analogous to the above discussion of hypochlorites and free available chlorine.

As noted above, due to the stability characteristics of such hypochlorite formulations, it would be expected that the concentration of hypochlorite will gradually drop over the given shelf-life (e.g., where shelf-stable is defined as a loss of no more than 25% hypochlorite, 20%, 10%, or other threshold drop when stored at 70° F.). Recognizing such, the formulation as initially manufactured and sold may have a concentration that that may be 25%, 20%, 10%, or similarly somewhat higher than any of the exemplary values shown in Table 1, such that after (e.g., a year) of storage, the hypochlorite concentration would be as shown. For example, at the typical 2000 ppm to 3000 ppm concentrations contemplated herein, one might expect a loss of about 500 ppm of hypochlorite over such a 1 year period of time, where the composition is stored undosed on any substrate, sealed in a pouch 108 of the packaged system, as described herein. A decomposition of 500 ppm of hypochlorite may drop the overall pH value of the formula by about 0.5 pH units, where a carbonate or other buffer is present at e.g., from 0.2% to less than 0.4%.

Figure 4A:
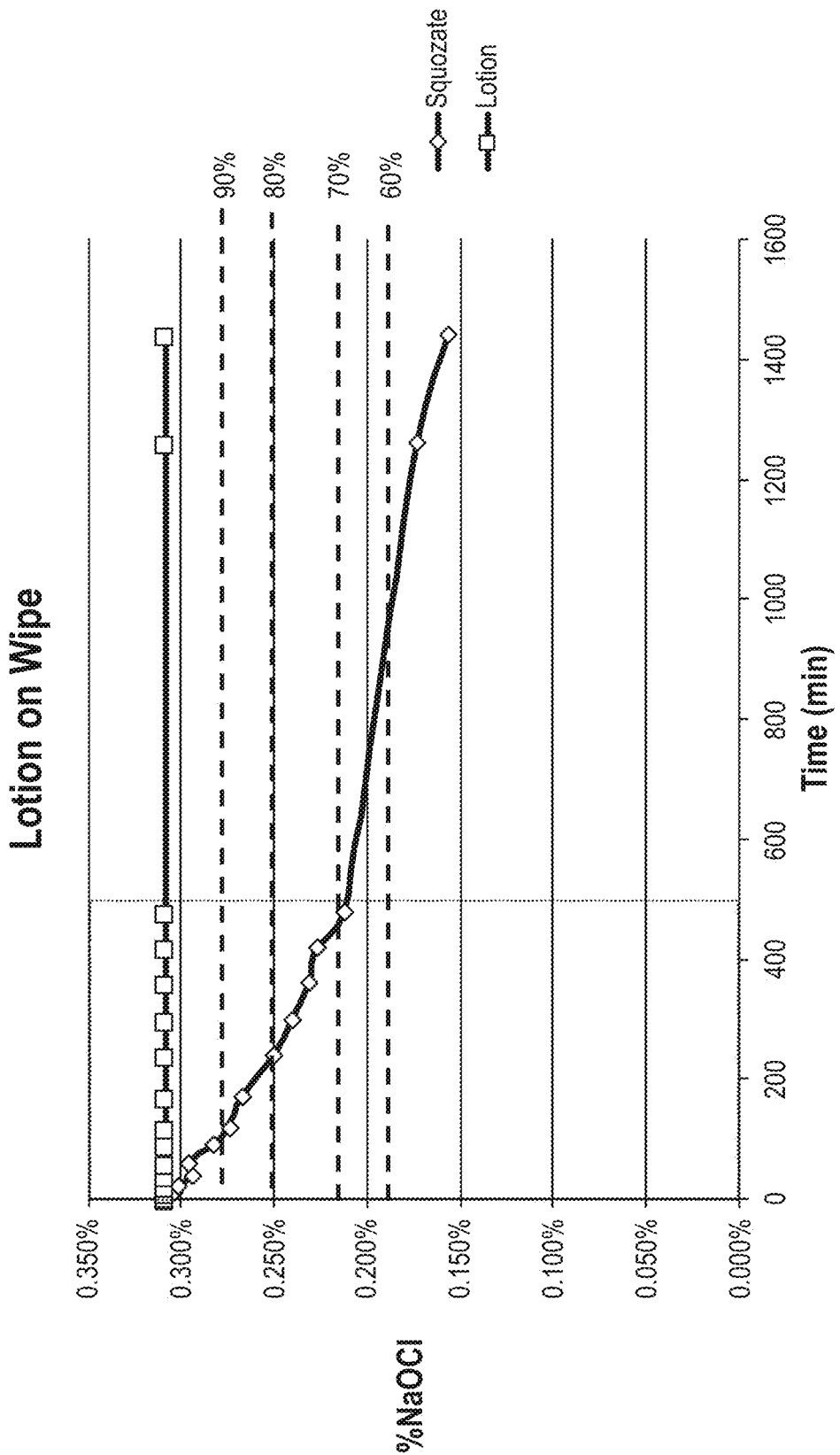
FIG. 4A shows stability results for an exemplary composition dosed onto a pulp containing wipe.

FIG. 4A shows stability data for an exemplary lotion (e.g., hypochlorite concentration of about 2500 to 3100 ppm, pH of 11.2), for the lotion alone (undosed), as well as how the concentration of hypochlorite quickly drops for the "squozate" to a value of only about 70% of its initial concentration after about 500 minutes (about 8 to 8.5 hours). The wipe used in the testing shown in FIG. 4A included significant pulp content (e.g., a 60/40 pulp/synthetic blend, with 60% pulp content). Thus, where packaged systems using synthetic wipes may provide for 30-180 days, 30-150 days, or 30-90 days of usable stability after dosing (i.e., providing the desired reduction in a population of C. diff or another target microbe), packaged systems with pulp containing wipes may provide for a usable stability that only extends for about 8 hours. It can thus be important that where the wipes include significant pulp content, that they be provided in a package that will be used up within the same day or work shift that the system and pack is activated.

Interestingly, the composition may thus be stable as stored within the burstable pouch (e.g., 108) to exhibit no more than a 30% loss of free available chlorine over a 12 month period, while at the same time, once dosed on the plurality of wipes, the composition may exhibit more than a 30% loss of free available chlorine over a 12 month period. For example, the system may be such that the composition may exhibit no more than a 25% loss of free available chlorine over a 12 month period before activation (when stored in pouch 108), but may exhibit more than a 30% loss of free available chlorine over a 24 hour period upon activation and dosing of the composition onto the wipes.

Figure 4B:
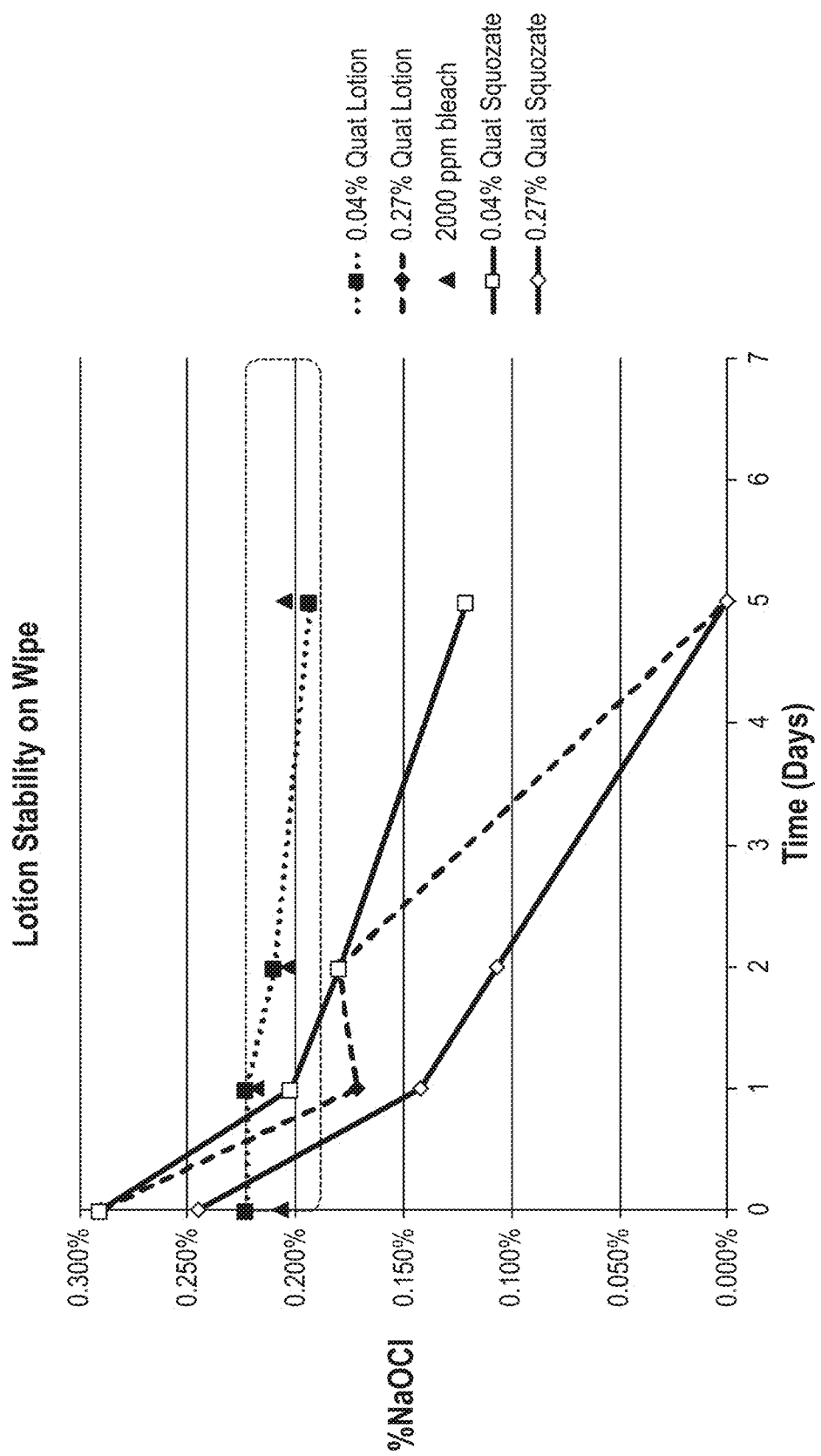
FIG. 4B shows stability results for another exemplary composition dosed onto a wipe.

FIG. 4B shows similar data as in FIG. 4A, but for slightly different compositions (e.g., 4000 ppm hypochlorite, and 2700 ppm hypochlorite), showing how the hypochlorite concentration drops for the lotion alone (un-dosed), and also showing the drop in hypochlorite concentration for the squozate. The dashed box in FIG. 4B shows one acceptable target threshold, centered around a concentration of approximately 2000 ppm hypochlorite, which can provide the desired microefficacy against C. diff, as well as other target microbes. The data in FIG. 4B shows acceptable efficacy for up to 8 hours, or even up to a 1-2 days.

Figure 5A:
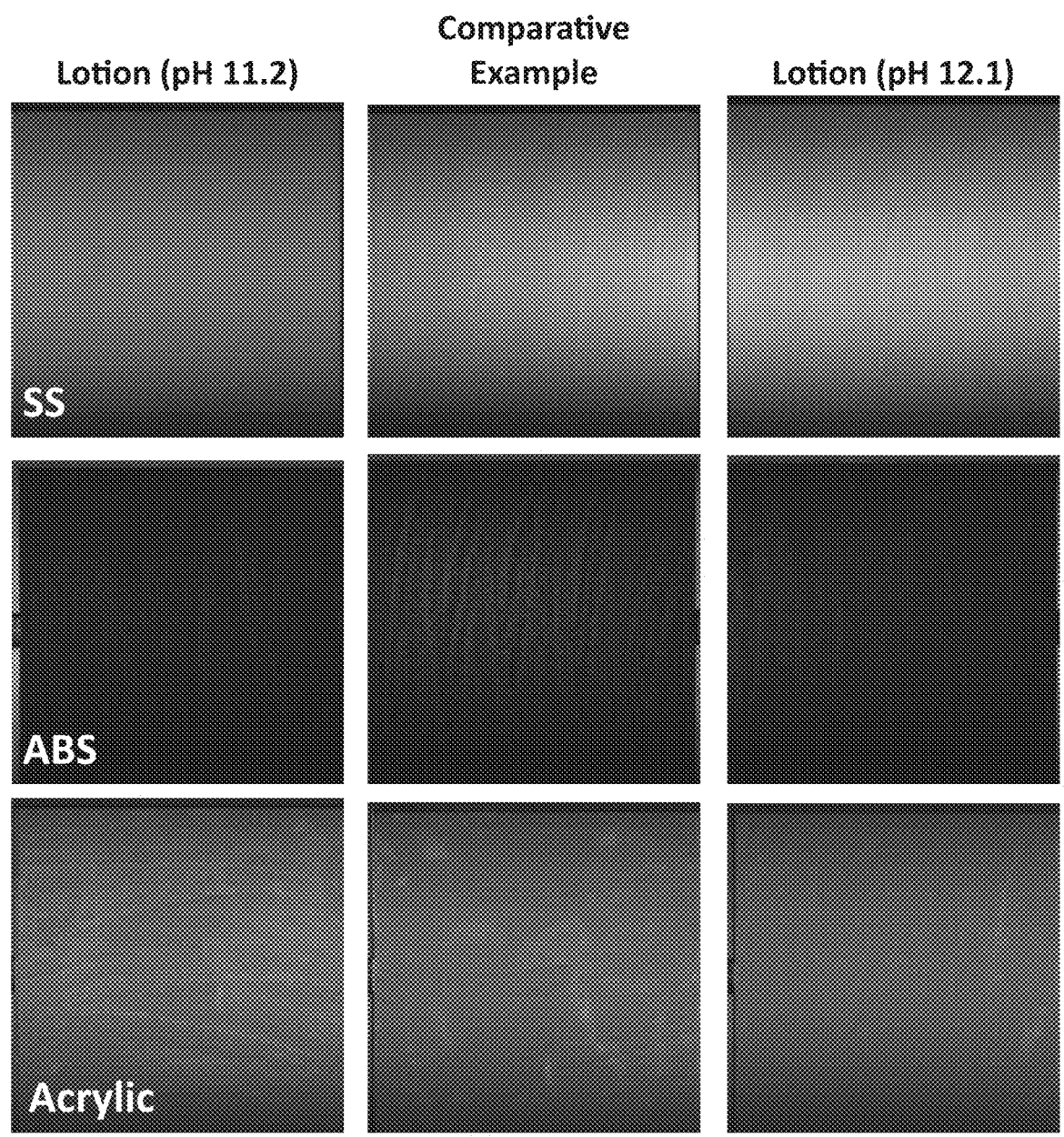
FIG. 5A shows residue (e.g., streaking and filming) results for two exemplary compositions as compared to a comparative composition.
Figure 5B:
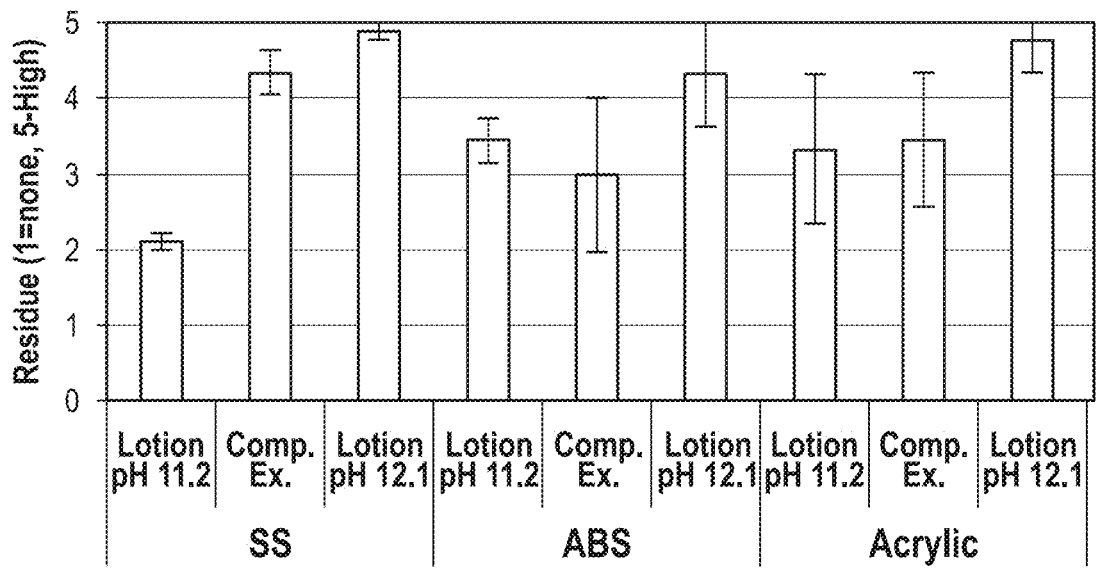
FIG. 5B charts residue (e.g., streaking and filming) results for the compositions tested in FIG. 5A.

FIGS. 5A-5B show the streaking and filming residue characteristics of tested exemplary compositions (e.g., 2500 ppm hypochlorite, 30 ppm of Ammonyx LO, 3000 ppm of a buffer, and 660 ppm of a silicate, pH 11.2) on stainless steel, ABS, and acrylic tiles. FIGS. 5A and 5B show residue results after 30 wipes, under standardized testing conditions, each for 3 compositions. One tested composition was as described herein, having low hypochlorite concentration (e.g., 2500 ppm hypochlorite, 30 ppm of Ammonyx LO, 3000 ppm of a buffer, and 660 ppm of a silicate), at a pH of 11.2. Another was otherwise similar, but at a pH of 12.1. These were compared to a commercially available product, also with pH greater than 12 (e.g., 12 to 12.5), with a hypochlorite concentration of 5500 ppm. The residue results shown in FIG. 5B show excellent results on stainless steel and acrylic, with near parity results on ABS, for the exemplary composition with a hypochlorite concentration of 2500, and a pH of less than 12 (e.g., 11.2).

Figure 6:
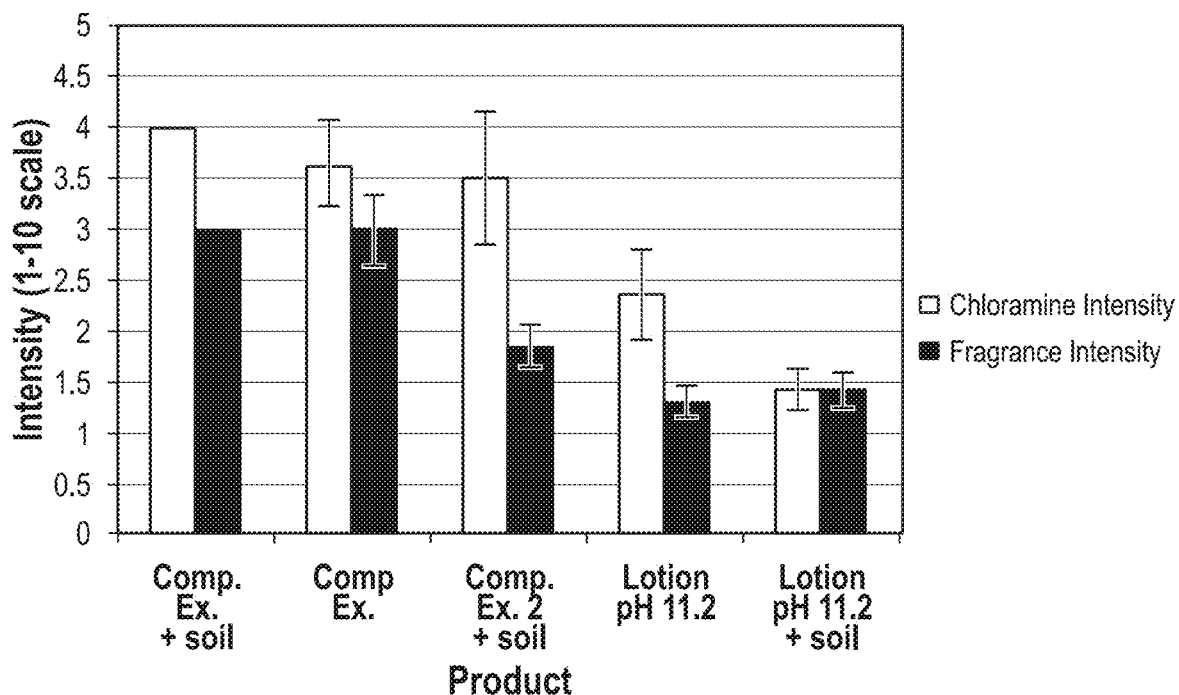
FIG. 6 charts evaluation of odor characteristics of an exemplary composition compared to comparative compositions.

FIG. 6 shows results of an odor evaluation for similar tested and comparative compositions, both with and without the presence of soil. The first comparative example shown at left is the same comparative composition (hypochlorite concentration of 5500 ppm, pH of 12-12.5) used in the residue testing. The "Comp. Ex. 2" in FIG. 6 is another commercially available composition, having a hypochlorite concentration of 6300 ppm, and a pH of 12.5. The exemplary tested composition (2500 ppm hypochlorite, 30 ppm of Ammonyx LO, 3000 ppm of a buffer, and 660 ppm of a silicate, pH 11.2) exhibited significantly lower odor intensity, both for chloramine as well as fragrance, or overall odor. The "bleach" odor associated with the exemplary formulation is so minor, many test subjects did not even realize the composition included hypochlorite.

Because the composition includes relatively low hypochlorite concentration, and lower pH (i.e., less than 12, such as 11 to 11.5), it also exhibits significantly improved surface compatibility, across a wide range of materials. For example, polycarbonate materials will often craze, crack, split, and even break upon prolonged exposure to elevated hypochlorite concentrations and/or pH values of 12 or greater. Table 2 below shows results of surface compatibility with these same tested compositions, by soaking in such compositions for a period of 2 weeks.

TABLE 2

| Composition | Surface | 24 Hr | 48 Hr | 72 Hr | 2 Wks |
| --- | --- | --- | --- | --- | --- |
| Ex. 1, pH 11.2 | PC | 0 | 0 | 2 | 2 |
|  | ABS | 0 | 0 | 0 | 0 |
| Comp. Ex. | PC | 1 | 2 | 3 | 4 |
|  | ABS | 0 | 0 | 0 | 0 |
| Ex. 1, pH 12.1 | PC | 2 | 2 | 3 | 4 |
|  | ABS | 0 | 0 | 0 | 0 |

0 = no effect
1 = craze
2 = crack
3 = split
4 = break

The results show a significant improvement in the surface compatibility on polycarbonate in particular. This benefit is particularly enhanced when not only the hypochlorite concentration is maintained below 5000 ppm (e.g., Ex. 1 had 2500 ppm), but where pH is also less than 12, as shown by the results.

Table 3 below shows a summary of evaluated surface compatibility, residue, odor, and microefficacy characteristics for the same compositions tested in Table 2.

TABLE 3

| Composition | Surface Safety | | Residue | | | Odor | C. Diff |
| --- | --- | --- | --- | --- | --- | --- | --- |
| | PC | ABS | SS | ABS | Acrylic | Odor | time |
| Comp. Ex. | Control | Control | Control | Control | Control | Control | 3 min |
| Ex. 1, pH 11.2 | + | Parity | + | Parity | Parity | + | 5 min |
| Ex. 1, pH 12.1 | − | Parity | − | − | − | | 5 min |

The summary of results show that the exemplary composition has improved surface safety, particularly with polycarbonate, while providing parity results with ABS. Residue performance is significantly better with stainless steel, while providing parity results with ABS and acrylic. The odor profile for the exemplary composition is significantly better than the comparative example. While the C. diff time to achieve a log 3 reduction is increased from 3 minutes to 5 minutes, this is in a formulation that is otherwise far more widely usable, e.g., on a wider variety of surfaces, and with significantly better odor characteristics. Such represents a significant advancement in the art. While tested in particular against C. diff (e.g., including C. diff spores), other target microbes against which efficacy may be provided include, but are not limited to, Pseudomonas, Trichophyton, Norovirus, M. bovis, and Staph.

Table 4 below shows another 24 compositions that may be exemplary of low hypochlorite concentration that may be suitable for use according to the present invention.

TABLE 4

| Sample | NaOCl (ppm) | SLS (wt %) | LO (wt %) | SXS (wt %) | EH-9 (wt %) | C10L (wt %) | BTC (wt %) | pH | R value |
| --- | --- | --- | --- | --- | --- | --- | --- | --- | --- |
| 2-1 | 2100 | — | — | — | — | — | — | 11.6 | — |
| 2-2 | 2100 | — | — | — | — | — | — | 10.3 | — |
| 2-3 | 2100 | 0.0508 | — | — | — | — | — | 11.6 | 0 |
| 2-4 | 2100 | 0.0508 | — | — | — | — | — | 10.3 | 0 |
| 2-5 | 2100 | — | 0.0516 | — | — | — | — | 11.6 | 1 |
| 2-6 | 2100 | — | 0.0516 | — | — | — | — | 10.3 | 1 |
| 2-7 | 2100 | — | 0.0252 | — | — | — | 0.027 | 11.6 | 1 |
| 2-8 | 2100 | — | 0.0288 | — | — | — | 0.027 | 10.3 | 1 |
| 2-9 | 2100 | — | — | — | 0.011 | — | — | 11.6 | 1 |
| 2-10 | 2100 | — | — | — | 0.0496 | — | — | 10.3 | 1 |
| 2-11 | 2100 | — | — | — | — | 0.0564 | — | 11.6 | 0 |
| 2-12 | 2100 | — | — | — | — | 0.0528 | — | 10.3 | 0 |
| 2-13 | 2100 | — | — | 0.051 | — | — | — | 11.6 | 0 |
| 2-14 | 2100 | — | — | 0.05 | — | — | — | 10.3 | 0 |
| 2-15 | 2100 | 0.0496 | — | 0.051 | — | — | — | 11.6 | 0 |
| 2-16 | 2100 | 0.0521 | — | 0.05 | — | — | — | 10.3 | 0 |
| 2-17 | 2100 | — | 0.0504 | 0.051 | — | — | — | 11.6 | 0.5 |
| 2-18 | 2100 | — | 0.0504 | 0.05 | — | — | — | 10.3 | 0.5 |
| 2-19 | 2100 | — | 0.0312 | 0.051 | — | — | 0.0304 | 11.6 | 0.55 |
| 2-20 | 2100 | — | 0.0336 | 0.05 | — | — | 0.0264 | 10.3 | 0.57 |
| 2-21 | 2100 | — | — | 0.051 | 0.0498 | — | — | 11.6 | 0.49 |
| 2-22 | 2100 | — | — | 0.05 | 0.051 | — | — | 10.3 | 0.5 |
| 2-23 | 2100 | — | — | 0.051 | — | 0.0552 | — | 11.6 | 0 |
| 2-24 | 2100 | — | — | 0.05 | — | 0.0564 | — | 10.3 | 0 |

LO = lauryl dimethyl amine oxide (Ammonyx LO)
SLS = sodium lauryl sulfate
SXS = sodium xylene sulfonate
EH-9 = ECOSURF EH-9, a nonionic alcohol ethoxylate surfactant
C10L = DOWFAX C10L, an anionic alkyldiphenyloxide disulfonate surfactant
BTC = BTC 1010, a cationic didecyl dimethyl ammonium chloride surfactant Table 5 below shows another 6 sample compositions that may be exemplary of low hypochlorite concentration that may be suitable for use according to the present invention.

TABLE 5

| Sample | NaOCl (wt %) | SLS (wt %) | Sodium Carbonate (wt %) | Sodium Silicate (wt %) | NaOH (wt %) | Water (wt %) | pH |
| --- | --- | --- | --- | --- | --- | --- | --- |
| 3-1 | 0.26-0.51 | 0.01 | 0.28-0.36 | 0.02-0.03 | 0.02-0.03 | balance | 11-12 |
| 3-2 | 0.27-0.34 | 0.01 | 0.28-0.36 | 0.02-0.03 | 0.02-0.03 | balance | 11-12 |
| 3-3 | 0.28-0.35 | 0.01 | 0.28-0.36 | 0.02-0.03 | 0.02-0.03 | balance | 11-12 |
| 3-4 | 0.29-0.36 | 0.01 | 0.28-0.36 | 0.02-0.03 | 0.02-0.03 | balance | 11-12 |

TABLE 5-continued

| Sample | NaOCl (wt %) | SLS (wt %) | Sodium Carbonate (wt %) | Sodium Silicate (wt %) | NaOH (wt %) | Water (wt %) | pH |
|---|---|---|---|---|---|---|---|
| 3-5 | 0.29-0.37 | 0.01 | 0.28-0.36 | 0.02-0.03 | 0.02-0.03 | balance | 11-12 |
| 3-6 | 0.34-0.43 | 0.01 | 0.28-0.36 | 0.02-0.03 | 0.02-0.03 | balance | 12 |

The microefficacy of one of the exemplary compositions from Table 5 against *C. diff* was tested, as described in Applicant's U.S. application Ser. No. 16/182,415, already incorporated by reference in its entirety. The results are sufficient to support a disinfection claim (e.g., a log 6 reduction) against *C. difficile* for 180 second contact time with a PET substrate.

TABLE 6

| Sample ID | % wt. ingredient | Wipe substrate | pH | Contact time (seconds) | *C. difficile* log reduction |
|---|---|---|---|---|---|
| 1 | 99.392% water 0.273% sodium hypochlorite 0.01% sodium lauryl sulfate 0.29% sodium carbonate 0.025% sodium silicate 0.01% sodium hydroxide | PET | 10.9 | 180 | 6.43 |

Any of the sanitizing or disinfecting compositions described herein may be provided in an amount in a burstable pouch (e.g., 108, 108', 208), relative to the mass of the packaged un-dosed wipes to result in a desired loading ratio of the composition into the wipes, once the system is activated. For example, the mass loading ratio of lotion to substrate may be from about 0.1:1 to about 10:1 by weight, such as from 2:1 to 6:1, or from 3:1 to 5:1 Once dosed, the wipes (or other substrates) may be employed as disinfecting or sanitizing wipes. Because of the good surface compatibility, the wipes are suitable for use on a wide variety of surfaces, e.g., configured for general use, rather than only for use on specific surfaces, or in specific areas (e.g., isolation rooms). It may also be possible to provide such a system for floor cleaning or other cleaning, in combination with various tools configured to attach to the wipe or substrate.

Without departing from the spirit and scope of the invention, one of ordinary skill can make various changes and modifications to the invention to adapt it to various usages and conditions. As such, these changes and modifications are properly, equitably, and intended to be, within the full range of equivalence of the following claims.

The invention claimed is:

1. A system for sanitizing or disinfecting, the system comprising:
A) a resealable package containing a plurality of initially dry wipes; and
B) a sanitizing or disinfecting composition contained within a burstable pouch, which is contained within the package but separate from the dry wipes, wherein the burstable pouch is configured to dose the plurality of initially dry wipes with the sanitizing or disinfecting composition upon bursting of the pouch containing the sanitizing or disinfecting composition, wherein the sanitizing or disinfecting composition comprises:

(a) from 0.05% to less than 0.5% by weight of free available chlorine as provided by a hypochlorite;
(b) at least one of:
i) a nonionic surfactant selected from the group consisting of an alcohol ethoxylate, an alcohol propoxylate, or an alkyl polyglucoside and
ii) a zwitterionic surfactant selected from the group consisting of lauramine oxide, decylamine oxide, or myristyl dimethylamine oxide,
wherein:
1) the composition has an R value that is greater than 0, where R is defined as the sum of the concentration of any nonionic or zwitterionic surfactants plus any cationic surfactants, divided by total surfactant concentration, wherein total surfactant concentration includes any surfactant aids;
2) the composition is free of anionic surfactants other than surfactant aids;
3) the composition has a pH from 8.5 to 11.8;
4) the sanitizing or disinfecting composition exhibits at least a 3-log reduction in a *C. diff* population within 10 minutes; and
5) the sanitizing or disinfecting composition exhibits no more than a 500 ppm reduction in hypochlorite concentration over a 1 year period, and/or no more than a 0.5 pH drop over 1 year when the composition is sealed within the pouch.

2. The system of claim 1, wherein:
the composition is stable as stored within the burstable pouch so as to exhibit no more than a 25% loss of free available chlorine over a 12 month period; and
the composition as dosed on the plurality of wipes exhibits no more than 30% loss of free available chlorine over a 24 hour period.

3. A method for sanitizing or disinfecting, the method comprising: providing a system comprising:
the resealable package of claim 1, containing the plurality of initially dry wipes and the sanitizing or disinfecting composition within the burstable pouch within the package, and
activating the system by bursting the pouch containing the sanitizing or disinfecting composition, so as to dose the initially dry wipes with the sanitizing or disinfecting composition; and using at least one of the dosed wipes to treat a surface.

4. The system of claim 1, wherein the sanitizing or disinfecting composition further comprises at least one cationic surfactant.

5. The system of claim 1, wherein the composition has a pH of from 11 to 11.5.

6. The system of claim 1, wherein the burstable pouch of the package comprises a burstable membrane that initially separates the sanitizing or disinfecting composition from the undosed wipes.

7. The system of claim 6, wherein the membrane comprises polyethylene.

8. The system of claim 1 wherein the hypochlorite is sodium hypochlorite.

9. The system of claim 1 wherein free available chlorine as provided by the hypochlorite is in a range from 0.1% to 0.4% by weight.

10. The system of claim 1 wherein free available chlorine as provided by the hypochlorite is in a range from 0.2% to 0.3% by weight.

* * * * *